(12) United States Patent
Salamone et al.

(10) Patent No.: US 8,852,648 B2
(45) Date of Patent: Oct. 7, 2014

(54) DELIVERY OF BIOLOGICALLY-ACTIVE AGENTS USING VOLATILE, HYDROPHOBIC SOLVENTS

(71) Applicant: Rochal Industries, LLP, San Antonio, TX (US)

(72) Inventors: Joseph Charles Salamone, San Antonio, TX (US); Xiaoyu Chen, San Antonio, TX (US); Ann Beal Salamone, San Antonio, TX (US); Katelyn Elizabeth Reilly, San Antonio, TX (US)

(73) Assignee: Rochal Industries, LLP, San Antonio, TX (US)

(*) Notice: Subject to any disclaimer, the term of this patent is extended or adjusted under 35 U.S.C. 154(b) by 0 days.

(21) Appl. No.: 14/058,997

(22) Filed: Oct. 21, 2013

(65) Prior Publication Data
US 2014/0127320 A1    May 8, 2014

Related U.S. Application Data

(60) Provisional application No. 61/723,113, filed on Nov. 6, 2012.

(51) Int. Cl.
| | | |
|---|---|---|
| *A61K 9/107* | (2006.01) | |
| *A61K 31/155* | (2006.01) | |
| *A61K 31/7036* | (2006.01) | |
| *A61K 47/34* | (2006.01) | |
| *A61K 33/38* | (2006.01) | |
| *A61K 33/30* | (2006.01) | |
| *A61K 31/4174* | (2006.01) | |
| *A61K 47/20* | (2006.01) | |
| *A61K 38/12* | (2006.01) | |
| *A61K 36/886* | (2006.01) | |
| *A61K 36/537* | (2006.01) | |
| *A61K 36/534* | (2006.01) | |

(52) U.S. Cl.
CPC ............ *A61K 9/107* (2013.01); *A61K 31/7036* (2013.01); *A61K 47/20* (2013.01); *A61K 33/30* (2013.01); *A61K 31/4174* (2013.01); *A61K 36/886* (2013.01); *A61K 36/537* (2013.01); *A61K 47/34* (2013.01); *A61K 31/155* (2013.01); *A61K 33/38* (2013.01); *A61K 36/534* (2013.01)
USPC ............ 424/618; 424/641; 514/2.3; 514/399; 514/635; 514/772.3; 514/772.4; 514/785

(58) Field of Classification Search
USPC ............ 424/618, 641; 514/2.3, 39, 399, 635, 514/772.3, 772.4, 785
See application file for complete search history.

(56) References Cited

U.S. PATENT DOCUMENTS

| | | | |
|---|---|---|---|
| 4,717,737 A | 1/1988 | Kern | |
| 4,719,235 A | 1/1988 | Kern | |
| 4,885,310 A | 12/1989 | Kern | |
| 4,987,893 A | 1/1991 | Salamone et al. | |
| 5,103,812 A | 4/1992 | Salamone et al. | |
| 6,383,502 B1 | 5/2002 | Dunshee et al. | |
| 7,795,326 B2 | 9/2010 | Salamone et al. | |
| 8,263,720 B1 | 9/2012 | Salamone et al. | |
| 2005/0269204 A1* | 12/2005 | Bryning | 204/452 |
| 2006/0165603 A1* | 7/2006 | Meakin et al. | 424/45 |
| 2011/0076244 A1 | 3/2011 | Hammer | |
| 2012/0208974 A1 | 8/2012 | Sambasivam et al. | |

FOREIGN PATENT DOCUMENTS

| | | |
|---|---|---|
| WO | 94/19000 | 9/1994 |
| WO | 2012/071251 | 5/2012 |

OTHER PUBLICATIONS

Zielinska et al. "Silver-doped TiO2 prepared by microemulsion method: Surface properties, bio- and photoactivity", Separation and Purification Technology, 72, 2010, 309-318.*
Nesamony et al. "IPM/DOSS/Water Microemulsions as Reactors for Silver Sulfadiazine Nanocrystal Synthesis", Journal of Pharmaceutical Sciences, vol. 94, No. 6, Jun. 2005.*
Malik, SN, et al., "Effect of surfactants on absorption through membranes III: effects of dioctyl sodium sulfosuccinate and poloxalene on absorption of a poorly absorbable drug, phenolsulfonphthalein, in rats," J Pharm Sci. Jun. 1975;64 (6):987-90.
Changez, Mohammed, et al., "Aerosol-OT Microemulsions as Transdermal Carriers of Tetracaine Hydrochloride," Department of Chemistry, Faculty of Science, Hamdard University, New Delhi 110062, India, 2000 by Marcel Dekker, Inc., pp. 507-512.
De, Tapas K., et al., "Solution behaviour of Aerosol OT in non-polar solvents," Adv. Colloid Interface Sci., 59, (1995), pp. 95-193.
Flynn, Peter F., "Multidimensional multinuclear solution NMR studies of encapsulated macromolecules," Progress in Nuclear Magnetic Resonance Spectroscopy, 45, (2004), pp. 31-51.

(Continued)

*Primary Examiner* — Johann R Richter
*Assistant Examiner* — Genevieve S Alley
(74) *Attorney, Agent, or Firm* — Duane Morris LLP; J. Rodman Steele, Jr.; Gregory M. Lefkowitz

(57) ABSTRACT

A composition and method adapted for delivery of hydrophilic, biologically-active agents are disclosed. The composition can include a reverse microemulsion formed from at least one hydrophilic, biologically-active agent solubilized by a hydrophobic reverse emulsion surfactant in a non-stinging, volatile, hydrophobic solvent. The non-stinging, volatile, hydrophobic solvent is selected from the group consisting of volatile linear and cyclic siloxanes, volatile linear, branched, and cyclic alkanes, volatile fluorocarbons and chlorofluorocarbons, liquid carbon dioxide under pressure, and combinations thereof. The reverse microemulsion can be an optically clear solution.

25 Claims, No Drawings

(56) References Cited

OTHER PUBLICATIONS

Gupta, Reeta R., et al., "AOT water-in-oil microemulsions as a penetration enhancer in transdermal drug delivery of 5-fluorouracil," Colloids and Surfaces B: Biointerfaces, 41, (2005), pp. 25-32.

Hogan, Daniel J., et al., "Adverse dermatologic reactions to transdermal drug delivery systems," Journal of American Academy of Dermatology, (1990), vol. 22, pp. 811-814.

Kitchens, Christopher L., et al., "Solvent Effects on AOT Reverse Micelles in Liquid and Compressed Alkanes Investigated by Neutron Spin-Echo Spectroscopy," J. Phys. Chem. B, (2006), 110, 20392-20400.

Lalanne, J. R., et al., "Transport Properties of Diluted Inverted Micelles and Microemulsions," The Journal of Physical Chemisty, (1987), vol. 87, No. 4, pp. 696-707.

Lindsay, Tammy J., et al., "Treating Diabetic Peripheral Neuropathic Pain," American Family Physician, vol. 82, No. 2, Jul. 15, 2010, pp. 151-158.

Oldfield, Christopher, "Enzymes in Water-in-oil Microemulsions ('Reversed Micelles'): Principles and Applications," Principles and Applications, Biotechnology and Genetic Engineering Reviews, 12:1, pp. 255-327., Dec. 1994.

Osborne, David, et al., "Skin Penetration Enhancers Cited in the Technical Literature," Pharmaceutical Technology, Nov. 1997, pp. 58-93.

Prausnitz, Mark R., et al., "Transdermal drug delivery," Nat Biotechnol., Nov. 2008; 26(11): 1261-1268.

Varshney, M., "Effects of AOT micellar systems on the transdermal permeation of glyceryl trinitrate," Colloids and Surfaces B: Biointerfaces, 13, (1999), pp. 1-11.

Wokovich, Anna M., "Transdermal drug delivery system (TDDS) adhesion as a critical safety, efficacy and quality attribute," European Journal of Pharmaceutics and Biopharmaceutics, 64, (2006), pp. 1-8.

Malmsten, Martin, (2002), "Surfactants and Polymers in Drug Delivery," Institute for Surface Chemistry and Royal Institute of Technology, Marcel Dekker, Inc., New York, Chapt. 5, pp. 133-159.

\* cited by examiner

DELIVERY OF BIOLOGICALLY-ACTIVE AGENTS USING VOLATILE, HYDROPHOBIC SOLVENTS

CROSS-REFERENCE TO RELATED APPLICATIONS

This application claims priority to U.S. Provisional Application No. 61/723,113, filed Nov. 6, 2012, the entirety of which is incorporated by reference herein.

FIELD OF INVENTION

Novel compositions are disclosed for topical application and delivery of hydrophilic, biologically-active agents in a microemulsion to and through the protective outer layer of a biological surface, wherein a biological surface includes those of humans, animals, viruses, protozoa, fungi, and bacteria. More specifically, hydrophilic, polar, biologically active agents that are solubilized by a reverse emulsion surfactant into a microemulsion, with or without added polymer, in non-stinging, volatile, hydrophobic solvents are disclosed. Transdermal delivery is augmented by the addition of a penetration enhancer.

BACKGROUND OF THE INVENTION

The delivery of biologically-active agents through a biological surface is a well-recognized method of treatment in controlled drug delivery. Such compounds are often delivered from a device to a skin surface, with transdermal delivery through the skin.

The treatment of the skin of humans and animals with topical drugs, antibiotics, antimicrobial agents, anti-infective agents, and pain-relieving agents is well known. In recent years transdermal delivery of biologically active substances has gained favor because of the controlled release of a minimalized concentration of the active agent. The initial systems for transdermal delivery pertained to patches containing small, lipophilic drugs, such as scopolamine, nicotine, estradiol, fentanyl, lidocaine and testosterone, as well as combination patches containing drugs for contraception and hormone replacement. Following the initial patch studies, transdermal chemical enhancers were studied, as well as noncavitational ultrasound and iontophoresis. More recent developments for penetrating the stratum corneum of the skin involve microneedles, thermal ablation, microdermabrasion, electroporation, and cavitational ultrasound. Since the inception of transdermal drug delivery patches, it is believed that more than one billion transdermal patches are manufactured each year. However, it has been difficult to exploit the transdermal route to deliver hydrophilic drugs (M. R. Prausnitz and R. Langer, Nat. Biotechnol., November, 26(11), 1261-1268 (2008)).

A commercially successful application for the use of a non-stinging, volatile, hydrophobic solvent on human and veterinary skin has been in the area of liquid adhesive bandages. These bandages are prepared from siloxy-containing hydrophobic and amphiphilic polymers admixed with volatile liquid polydimethylsiloxanes and volatile liquid alkanes (U.S. Pat. Nos. 4,987,893, 5,103,812, 6,383,502, and 8,263,720, the entireties of which are incorporated herein by reference). They have been reported to provide non-stinging, non-irritating liquid bandage coating materials after solvent evaporation that allow body fluid evaporation while protecting the body surface from further contamination and desiccation. Over time, these polymer coatings self-remove from the skin as healing occurs. Certain hydrophobic drugs, such as isopropyl xanthic disulfide, a fungicide, can dissolve directly in these hydrophobic, volatile solvents (U.S. Pat. No. 5,103,812) without the use of any additives. However, hydrophilic (e.g., polar or ionic) biologically-active agents, such as pharmaceutical drugs, antimicrobial agents, anti-infective agents, and pain-relieving agents are not soluble in the hydrophobic volatile solvents.

SUMMARY

A composition for transdermal delivery of biologically-active agents in a hydrophobic, volatile solvent containing a reverse emulsion surfactant that gives a water-in-oil microemulsion (w/o) of the biologically-active agents solubilized in the volatile, non-polar solvent is described. The composition can provide transdermal delivery of biologically-active substances that are inherently insoluble in the volatile, hydrophobic solvent by solubilizing them in a reverse microemulsion. The biologically active agents can be hydrophilic (e.g., polar or ionic) and be solubilized in the hydrophobic, volatile solvent via a reverse microemulsion.

As used herein, "biologically-active agents" has its standard meaning and includes chemical substances or formulations that beneficially affect human, animals, or plants or is intended for use in the cure, mitigation, treatment, prevention, diagnosis of infection or disease, or is destructive to or inhibits the growth of microorganisms. The phrases "biologically-active agents" and "active agents" are used interchangeably herein.

As used herein, "biological surface" has its standard meaning and includes the surface or outer layer of bacteria, fungi, protozoa, viruses, plants, animals, and humans.

As used herein, "surfactant" has its standard meaning and includes emulsifying agents, emulsifiers, and surface-active agents.

As used herein, "microemulsion" is has its standard meaning and includes thermodynamically stable mixtures of oil, water (and/or hydrophilic compound) and surfactant. Microemulsions include three basic types: direct (oil dispersed in water, o/w), reverse (water dispersed in oil, w/o) and bicontinuous. Microemulsions are optically clear because the dispersed micelles have a diameter that is less than the wavelength of visible light (e.g., less than 380 nanometers, less than 200 nanometers, or less than 100 nanometers) in diameter. In the absence of opacifiers, microemulsions are optically clear, isotropic liquids.

As used herein, "reverse microemulsion" refers to a microemulsion comprising a hydrophilic phase suspended in a continuous oil phase. A reverse microemulsion can include droplets of a hydrophilic phase (e.g., water, alcohol, or a mixture of both) stabilized in an oil phase by a reverse emulsion surfactant. In such instances, a hydrophilic active agent can be solubilized in the droplets. However, in other instances, the reverse microemulsion can be free of water and/or alcohol, and the hydrophilic active agent can be directly solubilized in the oil phase by the reverse emulsion surfactant.

As used herein, "hydrophilic" has its standard meaning and includes compounds that have an affinity to water and are usually charged or has polar groups in its structure that attract water. For example, hydrophilic compounds can be miscible in water.

As used herein, "free of water and/or alcohol" means that the composition includes less than 3 wt-% water and $C_1$-$C_4$ alkyl alcohols combined, or less than 2 wt-%, or less than 1 wt-%, or less than 0.5 wt-%, or less than 0.1 wt-%.

As used herein, "non-stinging" means that the formulation does not cause a sharp, irritatingly or smarting pain as a result of contact with a biological surface.

As used herein, "non-burning" means that the formulation does not cause a biological surface to increase in temperature.

The compositions described herein are particularly helpful for transdermal delivery of biologically-active agents, particularly those of a hydrophilic or polar nature, from a non-stinging, volatile solvent capable of penetrating the stratum corneum of the skin and other biological surfaces in order to rapidly provide the biological agent to a targeted area. Such a solvent is advantageous over other transdermal procedures because of the ease of percutaneous penetration, painless application, the extent of the surface area that can be covered, including all areas that flex or stretch, and the speed with which the biologically-active agent can penetrate the skin.

The solvent for solubilization of biologically-active agents is preferably volatile and hydrophobic, and more preferentially the solvent is non-stinging and non-burning to intact skin or to an open wound. Such solvents are particularly useful because they can be applied without causing discomfort to the patient and the low surface tension facilitates flow into crevices and difficult to reach areas. Furthermore, rapidly volatilize because of their low heat of vaporizations, which deposits the biologically-active substances solubilized in the volatile, hydrophobic solvent in a desired location. Preferred non-stinging, non-burning hydrophobic solvents include hexamethyldisiloxane (HMDS) (heat of vaporization 34.8 KJ/mol) and isooctane (heat of vaporization 33.26 kJ/mol), which can be used in spray-on applications on biological surfaces, many drugs are difficulty soluble or insoluble in these solvents. Silicone solvents are most preferred on the skin because they are non-stinging and give excellent lubrication and comfort. Of all the silicone fluids, hexamethyldisiloxane possesses the fastest evaporation rate, the lowest viscosity, and the lowest surface tension, with the highest spreadability. Additionally, unlike other volatile fluids, hexamethyldisiloxane does not heat, burn, or sting the skin as it evaporates, and only slight cooling is observed. Although these attributes make silicone solvents beneficial for topical treatment to skin, few biologically-active organic or inorganic substances dissolve in them without the microemulsion system described herein.

The hydrophobic, volatile liquid is preferably non-stinging and non-irritating, and comprises a low molecular weight polydimethylsiloxane, such as hexamethyldisiloxane, octamethyltrisiloxane, or an alkylmethyltrisiloxane; a low molecular weight cyclic siloxane, such as hexamethylcyclotrisiloxane or octamethylcyclotetrasiloxane; cyclomethicones, a linear, branched or cyclic alkane, such as propane, butane, and isobutane (under pressure), pentane, hexane, heptane, octane, isooctane, and isomers thereof, petroleum distillates, volatile vegetable hydrocarbons, cyclopentane or cyclohexane; a chlorofluorocarbon, such as trichloromonofluoromethane, dichlorodifluoromethane, and dichlorotetrafluoroethane; a fluorocarbon, such as tetrafluoroethane, heptafluoropropane, 1,1-difluoroethane, pentafluoropropane, perfluoroheptane, perfluoromethylcyclohexane, hydrofluoroalkanes such as 1,1,1,2,-tetrafluoroethane and 1,1,1,2,3,3,3-heptafluoropropane, combinations thereof and the like; a volatile gas under pressure, such as liquid carbon dioxide; or a mixture thereof. As will be understood, when stored under high pressure, carbon dioxide can be present in the form of a liquid at room temperature. The volatile solvent can be hexamethyldisiloxane, isooctane, and mixtures thereof. Preferentially, the volatile solvent is hexamethyldisiloxane.

As used herein, "volatile" has its standard meaning, that is, it can evaporate rapidly at normal temperatures and pressures. For example, a solvent is volatile if one drop (0.05 mL) of the solvent will evaporate completely between 20-25° C. within 5 minutes, or within 4 minutes, or within 3 minutes, or within 2 minutes, or within 1 minute, or within 30 seconds, or within 15 seconds.

The biologically-active agents can be solubilized in the hydrophobic volatile liquid by the addition of a reverse emulsion surfactant, such that a reverse microemulsion is formed. A reverse emulsion, also termed an inverse emulsion, results from the aggregation of surfactant molecules in a nonpolar solvent, wherein water is incorporated into the surfactant core, such that a water-in-oil emulsion is formed. Reverse emulsion surfactants with HLB numbers from 3 to 11 are generally used, where HLB is the hydrophile-lipophile balance. The HLB value of the reverse emulsion surfactants can range from 5 to 11 or 7 to 10. The higher the HLB number, the more water-soluble the surfactant, while a low HLB number indicates a lower aqueous solubility and a higher affinity for the non-polar phase.

In some embodiment, the compositions described herein can be active antimicrobial agents against at least one microbe selected from the group consisting of Gram negative bacteria, Gram positive bacteria, and fungi. In some embodiment, the compositions described herein can be active antimicrobial agents against at least two microbes selected from the group consisting of Gram negative bacteria, Gram positive bacteria, and fungi, while the compositions can be active antimicrobial agents against Gram negative bacteria, Gram positive bacteria, and fungi in other embodiments.

It is also possible to have a double emulsion, such as a water-in-oil-in-water emulsion or an oil-in-water-in-oil emulsion. Unless otherwise specified, "reverse emulsion" includes double emulsions. Reverse emulsion can be water-in-oil emulsions, except for double emulsions.

The ratio of drug to volatile liquid to surfactant to water can be such that the resulting solution remains optically clear. The reverse emulsion surfactant can have inherent solubility in the hydrophobic, volatile liquid and can solubilize water and/or the active agent into the reverse micelle, yielding an overall clear, transparent solution. When a soluble polymer is added to the composition, solution clarity is maintained, as is the clarity of the resulting polymer film which, after solvent evaporation adsorbs the surfactant encapsulated biologically-active agent in water and acts as the substrate for sustained, transdermal delivery. In certain instances, the addition of water is not necessary for solubilization of biologically-active agents by a reverse emulsion surfactant in a volatile, hydrophobic solvent.

Suitable reverse emulsion surfactants include sodium bis(2-ethylhexyl)sulfosuccinate, sodium bis(tridecyl)sulfosuccinate, bis(dialkyl)sulfosuccinate salts, copolymers of polydimethylsiloxane and polyethylene/polypropylene-oxide, polyoxypropylene (12) dimethicone, cetyl PEG/PPG-10/1 dimethicone, hexyl laurate and polyglyceryl-4-isostearate, PEG-10 dimethicone, sorbitan monolaurate, sorbitan monooleate, polyoxyethylenesorbitan trioleate, polyoxyethylene octyl phenyl ether, polyoxyethylene 10 cetyl ether, polyoxyethylene 20 cetyl ether, polyethylene glycol tert-octylphenyl ether, sodium di(2-ethylhexyl)phosphate, sodium di(oleyl)phosphate, sodium di(tridecyl)phosphate, sodium dodecylbenzenesulfonate, sodium 3-dodecylaminopropanesulfonate, sodium 3-dodecylaminopropionate, sodium N-2-hydroxydodecyl-N-methyltaurate, lecithin, sucrose fatty acid esters, 2-ethylhexylglycerin, caprylyl glycol, long chain hydrophobic vicinal diols of monoalkyl glycols, monoalkyl glycerols, or monoacyl glycerols, polyoxyl castor oil derivatives, polyethylene glycol hydrogenated castor oil, tetraethylene glycol dodecyl ether, potassium oleate, sodium oleate, cetylpyridynium chloride, alkyltrimethylammonium bromides, benzalkonium chloride, didodecyldimethylammonium bromide, trioctylmethylammonium bromide, cetyltrimethylammonium bromide, cetyldimethylethylammonium bromide, and the like, with or without added alkanols such as isopropanol, 1-butanol, and 1-hexanol, and combinations thereof. The reverse emulsion surfactants can be dialkylsulfosuccinate salts, such as sodium bis(2-ethylhexyl)sulfosuccinate.

Sodium bis(2-ethylhexyl)sulfosuccinate (Aerosol AOT, also called AOT, docusate sodium, DSS, Aerosol OT, and sodium 1,4-bis(2-ethylhexoxy)-1,4-dioxobutane-2-sulfonate) is a well-studied surfactant, which forms reverse micelles of well-defined structure in organic solvents (T. K. De, A. Maitra, Adv. Colloid Interface Sci. 59, 95 (1995)). It is a versatile double-tailed medicinal surfactant (S. N. Malik, D. H. Canaham, M. W. Gouda, J. Pharm. Sci. 64, 987 (1975)). It is the most widely used surfactant in reverse micelle encapsulation studies (P. F. Flynn, Prog. Nucl. Magn. Reson. Spectrosc. 45, 31-51 (2004)) and is a common ingredient in consumer products. AOT microemulsions generally give "inverted" micelles filled with water in a weakly polar oil consisting of alkanes (cyclohexane, isooctane, etc.) or aromatic molecules (J. R. Lalanne, B. Pouligny, and E. Sein, J. Phys. Chem., 87, 696-707 (1983)). The chemical structure of AOT imparts a well-balanced hydrophilic-lipophilic property. This unique feature of AOT allows the formation of alcohol-free reverse micellar and normal micellar aggregates in non-aqueous and aqueous media, respectively, without using any co-surfactant. AOT dissolves a considerable amount of water in oil and forms a stable reverse micellar system that is also known as water-in-oil microemulsion (R. R. Gupta, S. K. Jain, M. Varshney, Colloids and Surfaces B: Biointerfaces, 41, 25-32 (2005)). It interacts with penetration enhancers, as a non-volatile oil phase, for transdermal delivery of many biologically active agents (M. Varshney, T. Khanna, M. Changez, Colloids & Surfaces B 13, 1-11 (1999)). Also, AOT microemulsions have been reported to act as safe transdermal carriers (M. Changez and M. Varshney, Drug Devel. Industrial Phar., 26(5), 507-512 (2000)). AOT (also called docusate sodium) has been reported to have a HLB value of 10, a value supporting microemulsion formation (Pharmaceutical Suspensions: From Formulation Development to Manufacturing, A. K. Kulshreshtha, O. N. Singh, G. M. Wall, eds., "Pharmaceutical Development of Suspension Dosage Form, Y Ali, et al., 2009, Table 4.3, page 112).

Dialkylsulfosuccinates, such as sodium bis(2-ethylhexy) sulfosuccinate (AOT), have also been demonstrated to have antibacterial (against Gram positive microorganisms), antifungal and anti-viral properties (U.S. Pat. Nos. 4,717,737, 4,719,235 and 4,885,310). This effect would be expected to enhance the antimicrobial and anti-infective properties of the compositions described herein.

The biologically-active agents that can be incorporated into the surfactant reverse micelles include: antibiotics, antiseptics, anti-infective agents, antimicrobial agents, antibacterial agents, antifungal agents, antiviral agents, antiprotozoal agents, sporicidal agents, antiparasitic agents, peripheral neuropathy agents, neuropathic agents, analgesic agents, anti-inflammatory agents, anti-allergic agents, anti-hypertension agents, mitomycin-type antibiotics, polyene antifungal agents, antiperspirant agents, decongestants, anti-kinetosis agents, central nervous system agents, wound healing agents, anti-VEGF agents, anti-tumor agents, escharotic agents, anti-psoriasis agents, anti-diabetic agents, anti-arthritis agents, anti-itching agents, antipruritic agents, anesthetic agents, anti-malarial agents, dermatological agents, anti-arrhythmic agents, anticonvulsants, antiemetic agents, anti-rheumatoid agents, anti-androgenic agents, anthracyclines, anti-smoking agents, anti-acne agents, anticholinergic agents, anti-aging agents, antihistamines, anti-parasitic agents, hemostatic agents, vasoconstrictors, vasodilators, anticlotting agents, cardiovascular agents, angina agents, erectile dysfunction agents, sex hormones, growth hormones, immunomodulators, tumor necrosis factor alpha, anti-cancer agents, antineoplastic agents, anti-depressant agents, antitussive agents, anti-neoplastic agents, narcotic antagonistics, anti-hypercholesterolaemia agents, apoptosis-inducing agents, birth control agents, sunless tanning agents, emollients, alpha-hydroxyl acids, matrix metalloproteinases, topical retinoids, hormones, tumor-specific antibodies, antisense oligonucleotides, small interfering RNA (siRNA), anti-VEGF RNA aptamer, nucleic acids, DNA, vitamins, essential oils, silver salts, zinc salts, salicylic acid, benzoyl peroxide, 5-fluorouracil, nicotinic acid, nitroglycerin, clonidine, estradiol, testosterone, nicotine, motion sickness agents, scopolamine, fentanyl, diclofenac, buprenorphine, bupivacaine, ketoprofen, opiods, cannabinoids, enzymes, enzyme inhibitors, oligopeptides, cyclopeptides, polypeptides, proteins, prodrugs, protease inhibitors, cytokines, hyaluronic acid, chondroitin sulfate, dermatan sulfate, parasympatholytic agents, chelating agents, hair growth agents, lipids, glycolipids, glycoproteins, endocrine hormones, growth hormones, growth factors, heat shock proteins, immunological response modifiers, saccharides, polysaccharides, insulin and insulin derivatives, steroids, corticosteroids, and non-steroidal anti-inflammatory drugs or similar materials, in either their salt form or their neutral form, either being inherently hydrophilic or encapsulated within a hydrophilic microparticle or nanoparticle. Such biologically-active agents could be in either of the (R)-, (R,S)-, or (S)-configuration, or a combination thereof.

The non-stinging, hydrophobic volatile liquid can be a low molecular weight polydimethylsiloxane, such as hexamethyldisiloxane or octamethyltrisiloxane; a low molecular weight cyclic siloxane, such as hexamethylcyclotrisiloxane or octamethylcyclotetrasiloxane; a linear, branched or cyclic alkane, such as propane, butane, and isobutane (under pressure), pentane, hexane, heptane, octane, isooctane, petroleum distillates, or cyclohexane; a chlorofluorocarbon such as trichloromonofluoromethane, dichlorodifluoromethane, and dichlorotetrafluoroethane; a fluorocarbon such as tetrafluoroethane, heptafluoropropane, 1,1-difluoroethane, pentafluoropropane, perfluoroheptane, perfluoromethylcyclohexane, hydrofluoroalkanes such as 1,1,1,2,-tetrafluoroethane and 1,1,1,2,3,3,3-heptafluoropropane, combinations thereof and the like; a volatile gas under pressure, such as liquid carbon dioxide; or a mixture thereof. As will be understood, when stored under high pressure, carbon dioxide can be present in the form of a liquid at room temperature. The volatile solvent can be hexamethyldisiloxane, isooctane, and mixtures thereof. Preferably, the volatile solvent is hexamethyldisiloxane.

More hydrophilic solvents, such as ethanol, isopropanol, glycerin, propylene glycol, and poly(ethylene glycol) can be added in small amounts (10 weight % or less) to the reverse emulsion surfactant in the volatile, hydrophobic solvent in order to enhance solubility of the biologically active agent or any other added material, but these polar solvents should not interfere with the overall solvent composition being non-stinging to a user. The hydrophilic solvents can include ethanol, isopropanol, glycerin and mixtures thereof. Other hydrophilic solvents, such as methanol, acetone, dioxane, ethyl acetate, tetrahydrofuran, N-methylpyrrolidone, N,N-dimethylacetamide, tetraethylene glycol, dimethyl sulfoxide and mixtures thereof can also be used. The composition can be free of added hydrophilic solvents.

Chemical penetration enhancers are known to significantly enhance the transdermal delivery of drugs through the skin strata to the dermis. The penetration enhancer can function to enhance transdermal delivery of the biologically-active agent through the stratum corneum to the dermis, as well as potentially facilitating penetration of an antibiotic or antimicrobial agent through the outer wall of a microorganism (e.g., bacteria, mold, yeast, or protozoa), thus enhancing biocidal activity. Such penetration enhancers include, but are not limited, fatty acids such as branched and linear $C_6$-$C_{18}$ saturated acids, unsaturated acids, such as $C_{14}$ to $C_{22}$, oleic acid, cis-9-octadecenoic acid, linoleic acid, linolenic acid, fatty alcohols, such as saturated $C_8$-$C_{18}$ terpenes, such as d-limonene, alpha-pinene, 3-carene, menthone, fenchone, pulegone, piperitone, eucalyptol, chenopodium oil, carvone, menthol, alpha-terpineol, terpinen-4-ol, carveol, limonene oxide, pinene oxide, cyclopentane oxide, triacetin, cyclohexane oxide, ascaridole, 7-oxabicylco[2,2,1]heptane, 1,8-cineole, glycerol monoethers, glycerol monolaurate, glycerol monooleate, isostearyl isostearate pyrrolidones, such as 2-pyrrolidone, N-methyl-2-pyrrolidone, 1-ethyl-2-pyrrolidone, 5-methyl-2-pyrrolidone, 1,5-dimethyl-2-pyrrolidone, 2-pyrrolidone-5-carboxylic acid, N-hexyl-2-pyrrolidone, N-lauryl-2-pyrrolidone, 1-dodecylazacycloheptan-2-one, 4-decyloxazolidin-2-one, N-dodecylcaprolactam, and 1-methyl-3-dodecyl-2-pyrrolidone, cationic surfactants such as alkyltrimethylammonium halides, alkyldimethylbenzylammonium halides and alkylpyridinium halides, anionic surfactants, such as sodium lauryl sulfate and sodium laureth sulfate, and nonionic surfactants, such as polysorbates 20, 21, 80 and 81, Pluronic F127, Pluronic F68, N-n-butyl-N-n-dodecylacetamide, N,N-di-n-dodecylacetamide, N-cycloheptyl-N-n-dodecylacetamide and N,N-di-n-propyldodecanamide, urea, 1-dodecylurea, 1,3-didodecylurea, 1,3-diphenylurea, dimethyl sulfoxide, decylmethyl sulfoxide, tetradecylmethyl sulfoxide, hydrophobic esters such as methyl laureate, isopropyl lanolate, isopropyl myristate, isopropyl palmitate, and cyclodextrins. Also effective penetration enhancers include 1-alkyl-2-piperidinones, 1-alkyl-2-azacycloheptanones, such as 1-dodecyazacycloheptan-2-one, 1,2,3-alkanetriols, such as 1,2,3-nonanetriol, 1,2-alkanediols, n-alkyl-β-D-glucopyranosides, 2-(1-alkyl)-2-methyl-1,3-dioxolanes, oxazolidinones, such as 4-decyloxazolidin-2-one, N,N-dimethylalkanamides, 1,2-dihydroxypropyl alkanoates, such as 1,2-dihydroxypropyl decanoate, 1,2-dihydroxypropyl octanoate, sodium deoxycholate, trans-3-alken-1-ols, cis-3-alken-1-ols, and trans-hydroxyproline-N-alkanamide-C-ethylamide. A more complete list of penetration enhancers is given in "A Listing of Skin Penetration Enhancers Cited in the Technical Literature," D. W. Osborne, J. J. Henke, Pharmaceutical Technology, 21 (11), 58-66 (1997), the entirety of which is incorporated herein by reference. The penetration enhancers can include hydrophobic esters isopropyl myristate and isopropyl palmitate and non-ionic surfactants of polysorbate.

As a substrate carrier for the sustained release of the biologically-active agents incorporated within the reverse emulsion surfactant, with or without other additives, polymers utilized in non-stinging, liquid adhesive bandages are preferred. In some embodiments, liquid adhesive bandages are prepared from siloxy-containing hydrophobic polymers admixed with volatile liquid polydimethylsiloxanes and volatile liquid alkanes (U.S. Pat. Nos. 4,987,893, 5,103,812, and 8,263,720, the entireties of which are incorporated herein by reference, and U.S. Pat. No. 6,383,502) that provide non-stinging, non-irritating liquid bandage coating materials after solvent evaporation. Such coating materials are oxygen permeable and allow body fluid evaporation while protecting the body surface from further contamination and desiccation.

Additionally, amphiphilic siloxy-containing polymers have also been reported as liquid adhesive bandages in volatile, hydrophobic solvents (U.S. Pat. No. 7,795,326, the entirety of which is incorporated herein by reference), wherein the hydrophobic siloxysilane monomer is copolymerized with a hydrophilic nitrogen-containing monomer. Other siloxy-containing polymers include block copolymers of polydimethylsiloxane and polyurethane, and block copolymers of polydimethylsiloxane and poly(ethylene glycol). Still, other polymers soluble in the volatile, hydrophobic solvents include block copolymers of polystyrene and ethylene/butylene, block copolymers of polystyrene and polyisobutylene, block copolymers of polystyrene and polyisoprene, block copolymers of polystyrene and polybutadiene, block copolymers of polydimethylsiloxane and polyurethanes, polymers of $C_4$-$C_{18}$ acrylates and methacrylates, butyl rubber, polyisobutylene, and combinations thereof.

The preferred siloxy-containing monomer for both the hydrophobic and amphiphilic liquid adhesive bandages of the above mentioned patents is based upon the siloxy monomer, 3-methacryloyloxypropyltris(trimethylsiloxy)silane (TRIS). TRIS can be used in combination with both hydrophilic comonomers, such as N-isopropylacrylamide (NIPAM), or hydrophobic comonomers, such as methyl methacrylate, such that the resulting copolymers are soluble in a volatile, non-stinging, hydrophobic solvent.

Similarly, other polymer substrates could be based upon adhesive-type polymers from hydrophobic monomers such as isooctyl acrylate (ISO), such that they are soluble in volatile, non-stinging solvent.

In reference to the sustained release described herein, it is notable that certain diseases, such as peripheral neuropathy, are difficult to control because of the pain generated and the difficulty in predicting the extent to which a systemic drug would be effective. Current oral or systemic treatments for neuropathic pain include over-the-counter pain killers; tricyclic antidepressants, such as nortriptyline and amitriptyline; anticonvulsants, such as gabapentin, pregabalin, and carbamazepine; serotonin-norepinephrine reuptake inhibitors, such as duloxetine and venlafaxine; opiates such as oxycodone and tramadol; cannabinoids such as nitinol; and topical medications, such as the lidocaine patch and capsaicin cream. Although the over-the-counter pain killers and topical medications have minimal side effects, they also show limited ability to reduce neuropathic pain. Opiates are most effective and relatively inexpensive; however, they have a higher risk of addiction and induce tolerance and hyperalgesia with long-term use; hence, they are only used when other medications fail. Tricyclic antidepressants (TCAs) are effective and inexpensive, but could cause severe morbidity and mortality due to cardiovascular and neurological toxicity. Pregabalin and duloxetine are the only two drugs that are currently approved by the FDA for treatment of diabetic peripheral neuropathy. Although these drugs are relatively expensive, they are effective with fewer side effects, lower risk of abuse and drug tolerance, and fewer drug interactions compared to TCAs and opiates (T. J. Lindsay, B. C. Rodgers, V. Savath, K. Hettinger, Am. Fam. Physician, 82(2), 151-8 (2010)), although they may still have serious side effects.

Another important method of topical drug delivery is treating motion sickness through the use of a scopolamine transdermal patch, which is normally applied behind the ear. It has been reported that scopolamine delivered transdermally is associated with considerably fewer side effects than when administered by other routes (http://www.drugs.com/sfx/scopolamine-side-effects.html).

In the treatment of microbial infection on the skin by aerobic microorganisms or under the skin by anaerobic microorganisms, treatment is either by the utilization of antibiotics, predominantly through oral application, or by the use of topical antimicrobial agents or anti-infective agents, such as liquids, creams, or ointments. An antimicrobial agent is defined as a substance that kills microorganisms or inhibits their growth or replication, while an anti-infective agent is defined as a substance that counteracts infection by killing infectious agents, such as microorganisms, or preventing them from spreading. Often, the two terms are used interchangeably.

In general, antimicrobial agents (or anti-infective agents) such as chlorhexidine, poly(hexamethylene biguanide), alexidine, benzalkonium chloride, benzethonium chloride, cetyltrimethylammonium chloride, cetylpyridynium chloride, alkyltrimethylammonium bromides, neomycin, bacitracin, polymyxin B, miconazole, clotrimazole, peroxides, salicylic acid, salicylates, silver, silver salts, zinc salts, N-halo compounds and the like are utilized in topical formulations. A major problem for microbial infection on the surface of the skin surface or inside the body is the presence of a microbial biofilm, wherein the biofilm is an aggregate of microorganisms that are adhered to each other on a surface through an extracellular polymeric matrix. Biofilms are difficult to eradicate, and targeted delivery of an antimicrobial, biologically active substance will greatly increase its concentration to facilitate the biofilm's eradication.

Currently used transdermal delivery patches have a number of difficult issues associated with them due to long-term skin occlusion. These side effects include contact dermatitis, growth of bacteria and yeast, and painful removal of patches (Hogan, D. J., Maibach, H. I., "Adverse dermatologic reactions to transdermal drug delivery systems," J. Am. Acad. Dermatol., 22, 811-4 (1990)). Patches also have reduced efficacy due to issues with adhesion; temperature changes, perspiration, bathing, and movement, which cause patches to wrinkle or fall off the patient. Adhesion is a critical factor for successful drug delivery (Wokovich, A. M., Prodduturi, S., Doub, W. H., Hussain, A. S., Buhse, L. F., Eur. J. Pharm. Biopharm. 64, 1-8 (2006)).

The spray-on and paint-on coatings described herein (e.g., the compositions including soluble polymers) can alleviate a number of the difficulties with transdermal patches described above by providing a conformal coating with improved drug release consistency and efficiency as compared to current patch products. In addition, unlike microneedles and other methods of topical application, a spray-on application from a volatile, non-stinging solvent is less invasive and minimizes pain associated with application and delivery of biologically-active agents to the skin.

One of the benefits of the compositions described herein is that they can include a polymeric substrate for adsorption of the biologically-active agent which, after evaporation of the volatile solvent, provides sustained release of the biologically active agent to the biological surface on which it is deposited. In addition, the water-in-oil microemulsions of the compositions described herein exhibit slow release of the water-soluble biologically-active agents (Martin Malmsten, Surfactants and Polymers in Drug Delivery, 2002, Marcel Dekker, Inc. New York, Chapter 5, Microemulsions).

It is an object of the invention to provide delivery of biologically-active agents from a hydrophobic, volatile solvent to a biological surface.

It is a further object of this invention to provide a surfactant capable of solubilizing a biologically-active agent into a hydrophobic, volatile solvent.

It is a further object of this invention to provide a hydrophobic, volatile solvent that is non-stinging to a biological surface.

It is a further object of this invention to provide a reverse emulsion surfactant that also has antimicrobial properties.

It is a further object of the invention to provide transdermal delivery of biologically-active agents that are inherently insoluble in the hydrophobic, volatile solvent and are solubilized in a reverse emulsion.

It is a further object of the invention to provide transdermal delivery of biologically-active agents that can penetrate the skin surface to the epidermis.

It is a further object of the invention to provide transdermal delivery of biologically-active agents that can penetrate the skin surface to the dermis.

It is a further object of the invention to provide transdermal delivery of biologically-active agents that can penetrate the skin surface to the muscle.

It is a further object of the invention to provide transdermal delivery of biologically-active agents that can penetrate the skin surface to the bloodstream.

It is a further object of the invention that the volatile, hydrophobic solvent is non-stinging and non-irritating to skin.

It is a further object of the invention to provide a surfactant to solubilize biologically-active substances into a volatile, hydrophobic solvent.

It is an additional object to form a reverse microemulsion through the combination of a surfactant, a nonpolar solvent, and water to solubilize a biologically active agent.

It is an additional object to form a reverse microemulsion through the combination of a surfactant and a nonpolar solvent to solubilize a biologically active agent.

In another aspect of the invention, the reverse emulsion contains one or more solubilized polymers capable of forming an adherent coating on a biological surface after solvent evaporation.

In another aspect of the invention, the reverse emulsion contains a solubilized polymer incorporating the biologically active agent and reverse emulsion surfactant, which is capable of forming an adherent coating on a biological surface after solvent evaporation.

In another aspect of the invention, the reverse emulsion contains one or more percutaneous penetration enhancers.

In another aspect of the invention, the reverse emulsion contains one or more antimicrobial agents.

In another aspect of the invention, the reverse emulsion contains one or more anti-infective agents.

In another aspect of the invention, the reverse emulsion contains one or more peripheral neuropathy agents.

In another aspect of the invention, the reverse emulsion contains one or more motion sickness agents.

In another aspect of the invention, polymer coatings are provided that are useful for protecting biological surfaces against microbial contamination and form conformal, adhesive films after solvent evaporation.

In another aspect, the polymer coating functions as the substrate for sustained release of the biologically active agents.

In another aspect, a polymer coating is provided that is adherent under flex stress, including bending, twisting, and stretching.

It is a further object of the invention to provide a coating that, after application to skin and in the absence of a covering product, releases from that surface gradually over time without requiring externally applied solvents or other removal methods.

It is a further object of this invention to provide a coating that is water insoluble but is water vapor permeable.

It is a further object of this invention to provide a coating that is oxygen permeable.

It is a further object of the invention to provide a low surface tension polymer solution that will flow readily into confined spaces.

It is a further object to provide a polymer coating that can be cast upon the skin, mucous membranes, or internal organs.

In another aspect, a polymer coating is provided that remains adherent to a surface when exposed to external water, soaps, detergents, and most skincare products.

In another aspect, a polymer coating is provided that remains adherent to a surface when exposed to varying external humidity and temperature conditions.

In another aspect, a transparent polymer coating is provided that reduces pain and inflammation when applied to damaged or irritated skin or tissue.

In a further aspect of the invention, transdermal delivery of a drug for peripheral neuropathy is provided.

In a further aspect of the invention, transdermal delivery of an antibiotic is provided.

In a further aspect of the invention, transdermal delivery of an antimicrobial agent is provided.

In a further aspect of the invention, transdermal delivery of an antiseptic agent is provided.

In a further aspect of the invention, transdermal delivery of an anti-infective agent is provided.

In a further aspect of the invention, transdermal delivery of a pain-relieving agent is provided.

In a further aspect of the invention, transdermal delivery of an anti-inflammatory agent is provided.

In a further aspect of the invention, transdermal delivery of an anti-tumor agent is provided.

In a further aspect of the invention, transdermal delivery of a cardiovascular agent is provided.

In a further aspect of the invention, transdermal delivery of a diabetic agent is provided.

In a further aspect of the invention, transdermal delivery of a Parkinson's disease agent is provided.

In a further aspect of the invention, transdermal delivery of an Alzheimer's disease agent is provided.

In a further aspect of the invention, transdermal delivery of an attention deficit hyperactivity disorder agent is provided.

In a further aspect of the invention, transdermal delivery of insulin or an insulin derivative is provided.

In a further aspect of the invention, transdermal delivery of an opioid or cannabinoid is provided.

In a further aspect of the invention, transdermal delivery of a skin cancer agent is provided.

In a further aspect of the invention, transdermal delivery of an anti-cancer agent is provided.

In a further aspect of the invention, transdermal delivery of a dermatological agent is provided.

In a further aspect of the invention, transdermal delivery of a wound healing agent is provided.

In a further aspect of the invention, transdermal delivery of an anti-smoking agent is provided.

In a further aspect of the invention, transdermal delivery of an anti-psoriasis agent is provided.

In a further aspect of the invention, transdermal delivery of steroids, corticosteroids, and non-steroidal anti-inflammatory drugs is provided.

In a further aspect of the invention, transdermal delivery of an anti-diabetic agent is provided.

In a further aspect of the invention, transdermal delivery of an anti-allergic agent is provided.

In a further aspect of the invention, transdermal delivery of an antipruritic agent is provided.

In a further aspect of the invention, transdermal delivery of an anti-rheumatoid agent is provided.

In a further aspect of the invention, transdermal delivery of an erectile dysfunction agent is provided.

In a further aspect of the invention, transdermal delivery of an female sexual dysfunction agent is provided.

In a further aspect of the invention, transdermal delivery of a post-menopausal bone loss agent is provided.

In a further aspect of the invention, transdermal delivery of a urinary incontinence agent is provided.

In a further aspect of the invention, transdermal delivery of a vitamin, essential oil, or essential fatty acid is provided.

In a further aspect of the invention, transdermal delivery of a combination of one or more biologically-active agents is provided.

DETAILED DESCRIPTION

Transdermal drug delivery systems are typically systemically noninvasive, can be self-administered, can provide controlled extended release, and can improve patient compliance (M. R. Prausnitz, and R. Langer, Nat. Biotechnol., November, 26(11), 1261-1268 (2008)). However, currently used transdermal delivery patches have a number of issues associated with them due to long-term skin occlusion. These side effects include contact dermatitis, growth of bacteria and yeast, and painful removal of patches (Hogan, D. J., and Maibach, H. I., 1990, J. A. Acad. Dermat., 22, 811-814 (1990)). Patches also have reduced efficacy due to issues with loss of adhesion caused by temperature changes, perspiration, bathing, movement, skin lotions, and the like, which cause patches to wrinkle or fall off the patient (Wokovich, A. M., Prodduturi, S., Doub, W. H., Hussain, A. S., and Buhse, L. F., Eur. J. Pharm. Biopharm., 64, 1-8 (2006)). The spray-on or paint-on application of the compositions described herein provides a conformal coating that exhibits improved drug release consistency and efficiency as compared to current patch products.

Transdermal delivery of biologically-active agents from non-stinging, volatile solvents to and through the protective outer layer of a biological surface has surprisingly not been reported. An advantage of this method over other methods of transdermal drug delivery is that skin penetration can occur quickly because all active ingredients are solubilized into liquid form using a reverse emulsion surfactant that has the ability to coat and penetrate a biological surface.

The composition described herein is a unique liquid delivery system that can be brushed on, sprayed on, painted on, or used as a dipping solution; hence, allowing for the most skin surface coverage while minimizing additional pain inflicted during application. The hydrophobic portion of the delivery system preferably includes hexamethyldisiloxane (HMDS), a non-stinging, non-burning, quickly-evaporating hydrophobic solvent. The use of a volatile hydrophobic solvent enables an intimately conformal coating, which is particularly useful on peripheral and mobile areas such as fingers and toes. Unlike a patch, the intimately conformal coating may provide more consistent delivery of the biologically active substance over a larger area.

The biologically-active agents incorporated into the compositions described herein can include, but are not limited to, antimicrobial agents, anti-infective agents, antibacterial drug agents, antifungal drug agents, antiviral drug agents, anti-parasitic drugs, and pain medications. Antimicrobial and anti-infective agents can be incorporated in to the compositions. The antimicrobial and anti-infective agents include, but are not limited to, biguanides, such as poly(hexamethylene biguanide) (PHMB) hydrochloride and related salts, alexidine hydrochloride and related salts, chlorhexidine digluconate, chlorhexidine diacetate and related salts, nanosilver, colloidal silver, silver sulfadiazine, silver nitrate, hydrogen peroxide, benzoyl peroxide, peracetic acid, lactic acid, fatty acids, ethanol, isopropanol, long-chain alcohols, branched and long-chain glycols and glycerol ethers and esters, essential oils, benzalkonium chloride, benzethonium chloride, methylbenzethonium chloride, cetyltrimethylammonium bromide, cetylpyridinium chloride, honey, boric acid, benzoic acid, povidone-iodine, poloxamer-iodine, iodine, salicylic acid, zinc salts, tin salts, aluminum sulfate, bismuth subsalicylate, clotrimazole, miconazole nitrate, ketoconazole, fluconazole, oxiconazole nitrate, methyl salicylate, triethanolamine salicylate, phenyl salicylate, acetylsalicylic acid, thymol, eucalyptol, menthol, eugenol, peppermint oil, sage oil, chloroxlyneol, cloflucarban, hexylresorcinol, triclocarban, hexachlorophene, pyrithione zinc, chlorobutanol, capsaicin, warfarin, bacitracin, neomycin sulfate, polymyxin b sulfate, aloe vera, glutaraldehyde, formaldehyde, ethylene oxide, chloroamines, Dakin's solution, dilute bleach, polyquaternium-1, polyquaternium-10, ionene polymers, pyridinium polymers, imidazolium polymers, diallyldimethylammonium polymers, acryloyl-, methacryloyl-, and styryl-trimethylammonium polymers, acrylamido- and methacrylamido-trimethylammonium polymers, and antimicrobial peptides. The antimicrobial agents can include PHMB and its salts, alexidine and its salts, chlorhexidine and its salts, branched and long-chain glycols and glycerol ethers and esters, benzalkonium chloride, benzethonium chloride, cetyltrimethylammonium bromide, miconazole nitrate, and neomycin sulfate. The antimicrobial agents can be PHMB and its salts, chlorhexidine and its salts, miconazole nitrate, polymyxin b sulfate and neomycin sulfate.

Antibacterial drug agents that can be incorporated into the surfactant reverse micelles include, but are not limited to, penicillin-related compounds including beta-lactam antibiotics, broad spectrum penicillins, and penicillinase-resistant penicillins (such as ampicillin, ampicillin-sublactam, nafcillin, amoxicillin, cloxacillin, methicillin, oxacillin, dicloxacillin, azocillin, bacampicillin, cyclacillin, carbenicillin, carbenicillin indanyl, mezlocillin, penicillin G, penicillin V, ticarcillin, piperacillin, aztreonam and imipenem, cephalosporins (such as cephapirin, cefaxolin, cephalexin, cephradine and cefadroxil, cefamandole, cefoxitin, cefaclor, cefuroxime, cefuroxime axetil, cefonicid, cefotetan, ceforanide, cefotaxime, ceftizoxime, ceftriaxone, cefoperazone and ceftazidime), tetracyclines (such as tetracycline hydrochloride, demeclocytetracycline, doxycycline, methacycline, minocycline and oxytetracycline), beta-lactamase inhibitors (such as clavulanic acid), aminoglycosides (such as amikacin, gentamicin C, kanamycin A, neomycin B, netilmicin, streptomycin and tobramycin), chloramphenicol, erythromycin, clindamycin, spectinomycin, vancomycin, bacitracin, isoniazid, rifampin, ethambutol, aminosalicylic acid, pyrazinamide, ethionamide, cycloserine, dapsone, sulfoxone sodium, clofazimine, sulfonamides (such as sulfanilamide, sulfamethoxazole, sulfacetamide, sulfadiazine, and sulfisoxazole), trimethoprim-sulfamethoxazole, quinolones (such as nalidixic acid, cinoxacin, norfloxacin and ciprofloxacin), methenamine, nitrofurantoin and phenazopyridine. Pharmaceutical antimicrobial drug agents include agents active against protozoal infections, such as chloroquine, emetine or dehydroemetine, 8-hydroxyquinolines, metronidazole, quinacrine, melarsoprol, nifurtimox, and pentamidine.

Antifungal pharmaceutical and non-pharmaceutical drug agents that can be incorporated into the surfactant reverse micelles include, but are not limited to, amphotericin-B, flucytosine, ketoconazole, miconazole, itraconazole, griseofulvin, clotrimazole, econazole, terconazole, butoconazole, terbinafine, ciclopirox olamine, haloprogin, toinaftate, naftifine, nystatin, natamycin, anidulafungin, caspofungin, griseofulvin, Iodoquinol, undecylenic acid, benzoic acid, salicylic acid, propionic acid and caprylic acid.

Antiviral drug agents that can be incorporated into the surfactant reverse micelles include, but are not limited to, zidovudine, acyclovir, ganciclovir, vidarabine, idoxuridine, trifluridine, foxcarnet, amantadine, rimantadine, tee tree oil, and ribavirin.

Anti-parasitic drugs that can be incorporated into the surfactant reverse micelles include, but are not limited to, metronidazole, mebendazole, albendazole, milbemycin, ivermectin, praziquantel, artemisinin, quinine, chloroquine, halofantrine, mefloquine, lumefantrine, amodiaquine, pyronaridine, piperaquine, primaquine, tafenoquine, atovaquone, artemether, artesunate, dihydroartemisinin, artemisinin, proguanil, tetracyclines, pentamidine, suramin, melarsoprol, amphotericin, eflornithine, benznidazole, and aminosidine, Pain medications that can be incorporated into the surfactant reverse micelles include, but are not limited to, nortriptyline and amitriptyline; anticonvulsants such as gabapentin, pregabalin, and carbamazepine; serotonin-norepinephrine reuptake inhibitors such as duloxetine and venlafaxine; opiates such as oxycodone and tramadol; cannabinoids such as nitinol; and topical medications such as the lidocaine patch and capsaicin cream.

The solubilities of the above described drugs in water can be enhanced by salt formation, or by encapsulation within a hydrophilic matrix, such as a microparticle or nanoparticle utilizing a hydrophilic polymer covering. While not necessary for practicing the invention, when cationic, biologically-active agents are utilized in a volatile, hydrophobic solvent with a reverse emulsion surfactant such as sodium bis(2-ethylhexyl)sulfosuccinate (AOT), it is believed that a complex first forms between the cationic portion of the biologically-active agent and the anion of bis(2-ethylhexyl)sulfosuccinate, which complex is then encapsulated by dissolution into an AOT reverse micelle. Similarly, if an anionic biologically active agent is employed, a cationic reverse emulsion surfactant could generate an analogous complex. If a neutral reverse emulsion surfactant is used, either cationic, neutral, or anionic biologically active agents can be encapsulated into the reverse emulsion micelle, presumably without an ionic complex formation. Furthermore, anionic biologically active agents can also be encapsulated into an anionic reverse emulsion surfactant such as sodium bis(2-ethylhexyl)sulfosuccinate (AOT) without an insoluble complex first forming.

The reverse emulsion surfactants can be dialkylsulfosuccinates and salts thereof, with or without added water or alcohol. The dialkylsulfosuccinate salts range in hydrocarbon chain length of each alkyl group from 6 carbon atoms to 18 carbon atoms in length, and contain one or two identical or different, straight-chain and/or branched-chain, saturated or unsaturated alkyl groups. Exemplary, dialkylsulfosuccinates include, but are not limited to, sodium bis(2-ethylhexyl)sulfosuccinate (Aerosol AOT or AOT) and sodium bis(tridecyl) sulfosuccinate (Aerosol TR or TR). The anionic surfactant sodium bis(2-ethylhexyl)sulfosuccinate can form stable microemulsions consisting of water, AOT, and a bulk organic solvent (C. L. Kitchens, D. P. Bossev, and C. B. Roberts, J. Phys. Chem. B, 110, 20392-20400 (2006)).

In this invention, if water is needed, typically the amount of water forming the water-in-oil emulsion is between from about 0 to about 10 weight %, preferably between from about 0.001 to about 7.5 wt %, and more preferably from 0.01 to about 5 wt %. A minimum amount of water is most preferred to allow faster evaporation of the solvent. If an alcohol, such as ethanol, is added as a cosolvent, the alcohol concentration is 10% or less of the hydrophilic liquid (e.g., water plus alcohol). Alcohol can be used to enhance the solubility of the biologically-active agent in water for encapsulation by the reverse emulsion surfactant. In certain instances, the biologically-active agent may dissolve directly into the reverse emulsion surfactant in the volatile, non-polar solvent, even though the agent is inherently insoluble in the volatile, hydrophobic solvent.

The reverse emulsion surfactant can be present in an amount from 0.10 to 50 weight percent (wt %), or between 0.20 to 20 wt %, or between 0.40 to 10 wt % of the composition, or any combination thereof (e.g., 0.10-0.40 wt-% and 0.20-10 wt-%).

The biologically-active agent component of the formulation can be present in amounts ranging from 0.00001 to 10 wt %, or from 0.0001 to 7.5 wt %, or from 0.001 to 5 wt %, or from 0.01 to 2.5 wt %, or from 0.1 to 1 wt % of the composition, or any combinations thereof (e.g., 0.01-1 wt-% or 1-5 wt-%).

The volatile, hydrophobic solvent of the formulation can be present from 40 to 99.99 wt %, or from 45 to 99 wt %, or from 50 to 90 weight %, or from 55 to 80 weight percent of the composition, or any combination thereof (e.g., 40-55 wt-% or 45-80 wt-%).

The polar solvent (e.g., water and/or $C_1$-$C_4$ alkyl alcohols combined) can be present from 0 to 3 wt % or 0.01 to 3 wt %, or less than 2 wt %, or less than 1 wt %, or less than 0.5 wt %, or less than 0.1 wt %.

The added polymer, to form a substrate for the sustained release of the biologically-active agent over time, and which forms a coating on a biological surface after the evaporation of the volatile solvent, can be present in an amount ranging from 0 to 20 wt %, or from 1 to 15 wt %, or from 2 to 10 wt % of the composition, or any combination thereof (e.g., 2-15 wt % or 1-2 wt %).

The composition can include from 50-99.5 wt % volatile, hydrophobic solvent, 0.25 to 50 wt % reverse emulsion surfactant, from 0.00001 to 5 wt % of biologically active agent, and from 0 to 20 wt % polymer substrate. The composition can include from 0 to 5 wt % of a hydrophilic solvent (e.g., water and $C_1$-$C_4$ alkyl alcohols). The polymer substrate can be present in an amount that it is completely soluble in the composition and/or completely soluble in the volatile, hydrophobic solvent. The composition can be optically clear.

The following ingredients and their abbreviations are used in this invention:

ALEX: Alexidine Dihydrochloride, 1,1'-hexamethylenebis [5-(2-ethylhexyl)biguanide]dihydrochloride, Toronto Research Chemicals.

$AgNO_3$: Silver Nitrate, Alfa Aesar.

AOT: Aerosol AOT, sodium bis(2-ethylhexyl)sulfosuccinate, docusate sodium, Fisher Scientific.

Cavilon: 3M™ Cavilon™ No-Sting Barrier Film, composed of HMDS (65-90%), ISO (8-12%), Acrylate Terpolymer (3-12%), and polyphenylmethylsiloxane copolymer (0.1-5%).

CHG: Chlorhexidine Digluconate, Spectrum Chemicals.

CHG-P: Chlorhexidine powder, from neutralization and drying of chlorhexidine digluconate.

DULOX: Duloxetine, (+)-(S)-N-methyl-3-(naphthalen-1-yloxy)-3-(thiophen-2-yl)propan-1-amine, SST Corporation, and converted to the hydrochloride salt.

ETOH: Ethanol, VWR International.

G 67: Gransurf 67, PEG-10 dimethicone, Grant Industries.

G W9: Gransurf W9, Cetyl PEG/PPG-10/1 Dimethicone, hexyl laurate and polyglyceryl-4-isostearate, Grant Industries.

GML: Glycerol Monolaurate, Lauricidin®, Med-Chem Laboratories.

HMDS: Hexamethyldisiloxane, Dow Corning.

IOA: Isooctyl Acrylate, Sartomer.

IOA:NIPAM: 4:1 wt % Copolymer of IOA and NIPAM prepared by free radical polymerization (uncrosslinked); Table 1, US Patent Application Publication 2012/0208974.

IPM: Isopropyl Myristate, Alzo International Incorporated

IPP: Isopropyl Palmitate, Alzo International Incorporated.

ISO: Isooctane, VWR International.

Kraton: Kraton G1657 M, Kraton Performance Polymers, a linear triblock copolymer of styrene and ethylene/butylene, with a polystyrene content of 13%.

LIDO: Lidocaine Hydrochloride, 2-(diethylamino)-N-(2,6-dimethylphenyl)acetamide hydrochloride, Midcoast Environment.

MICON, Miconazole Nitrate, Sigma Aldrich.

MMA: Methyl Methacrylate, Alfa Aesar.

NEO: Neomycin Trisulfate, Sigma Aldrich.

Neosporin: Bacitracin, Neomycin, and Polymyxin B, Johnson & Johnson.

NIPAM: N-isopropylacrylamide, Jarchem.

PHMB: Poly(hexamethylene biguanide) Hydrochloride, Cosmocil™ CQ, Arch Chemical.

POLYMYX: Polymyxin B Trisulfate, Sigma Aldrich.

PREG: Pregablin, SST Corporation; converted to pregabalin hydrochloride; (S)-3-(aminomethyl)-5-methylhexanoic acid hydrochloride.

Roccal: Roccal®-D PLUS, Pfizer: a mixture of alkyldimethylbenzyl ammonium chloride, didecyldimethylammonium chloride, benzylcocoalkyldimethylammonium chlorides, and tributyltin oxide.

R-Surf: Reverse emulsion surfactant.

SC 50: Sensiva® SC 50, glycerol 1-(2-ethylhexyl) ether), Schülke & Mayr.

SCOP: Scopolamine Hydrochloride, Enzo Biochem.

SL: Sodium Laurate, sodium dodecanoate, Sigma Aldrich.

SORB: Sorbic Acid, 2,4-hexadienoic acid, Alfa Aesar.

TR: Aerosol TR, sodium bis(tridecyl)sulfosuccinate, Cytec Industries.

TRIS (containing 0.3% TRIS-D): 3-Methacryloxypropyltris (trimethylsiloxy)silane, Silar Laboratories.

TRIS dimer (TRIS-D): 1,3-Bis(3-methacryloxypropyl)-1,1,3,3-tetrakis(trimethylsiloxy)disiloxane, Gelest.

TRIS:MMA: 9:1 wt % copolymer of TRIS and MMA.

TRIS:NIPAM: 3:1 wt % copolymer of TRIS and NIPAM; U.S. Pat. No. 7,795,326.

Water: (Purified, USP), Ricca Chemical Company.

XL-TRIS: polymer of TRIS and MMA crosslinked with TRIS-D, TRIS/MMA/TRIS-D=60/20/20 wt % (U.S. Pat. No. 8,263,720).

$Zn(OAc)_2$: Zinc Acetate, Alfa Aesar.

EXAMPLES

For all formulations in the following Examples, each biologically-active agent was inherently insoluble in the non-polar, hydrophobic solvents tested, namely, isooctane (ISO) and hexamethyldisiloxane (HMDS). Solubility occurred in the presence of a reverse emulsion surfactant, with or without the presence of added water, to give optically clear, homogeneous solutions. Since the concentrations of the biologically-active agents (Active) were considerably less than that of the solvent used, the data in the Tables pertaining to all ingredients were rounded-off to the next highest number.

Table 1 lists the compositions of formulations in weight percent (wt %) of various antimicrobial agents often used in over-the-counter formulations solubilized as optically clear, transparent solutions in the non-stinging, volatile solvents of hexamethyldisiloxane (HMDS) and isooctane (ISO), with Aerosol AOT (AOT, HLB 10) as the reverse emulsion surfactant and water. The antimicrobial agents include three biguanides, poly(hexamethylene biguanide) hydrochloride (PHMB), alexidine dihydrochloride (ALEX), and chlorhexidine digluconate (CHG), as well as neomycin trisulfate (NEO), an aminoglucoside antibiotic, polymyxin B trisulfate (POLYMYX), a cyclic peptide antibiotic, and two antimicrobial salts, silver nitrate and zinc acetate. In addition, an ALEX formulation also included ethanol as a hydrophilic co-solvent with water because of the limited solubility of alexidine dihydrochloride in water.

All the hydrophilic, ionic, polar antimicrobial agents studied are inherently insoluble in ISO and HMDS. The antimicrobial activity of each of these agents is dependent upon their cationic form, and each is insoluble in the non-polar solvents of ISO and HMDS. However, these non-polar solvents containing AOT dissolve antimicrobial compounds that are soluble in water or alcohol. For the studied compounds of PHMB, CHG, ALEX, NEO, silver nitrate, zinc acetate, and POLYMYX, when these compounds were mixed with a higher concentration of AOT in HMDS or isooctane, a white precipitate initially formed, which then dissolved to form a clear solution upon increasing AOT content. Presumably, the cationic, biologically active agent formed a bis(2-ethylhexyl) sulfosuccinate salt with the AOT anion, which was then solubilized by Aerosol AOT into a reverse emulsion.

The amount of biologically active agent that can be incorporated appears to depend on the amount of water that can be dissolved in the AOT reverse emulsion in HMDS and ISO, which appears related to its solubility in water. For example, the water solubility of alexidine HCl (ALEX, 0.1% soluble in water) is much lower than CHX digluconate (CHG, 20% soluble in water). Thus, less ALEX can be solubilized in a reverse emulsion into the non-polar solvents with AOT. However, since ALEX is more soluble in ethanol than in water, adding ethanol increased its solubility in isooctane with AOT (Table 1).

Table 1 demonstrates that homogeneous, transparent (optically clear), stable solutions can be prepared from the various cationic antimicrobial agents studied in a reverse emulsion with the surfactant AOT in volatile, hydrophobic solvents. If said formulations are applied to a biological surface, after solvent evaporation the active agent would be transported to a biological surface.

From Table 1 it is seen that the weight percent of volatile solvent in each case was above 90%, with the amount of AOT ranging from approximately 0.5% to 5% of the formulation. Table 1 also includes two ratios, AOT/Active, where the active represents the cationic antimicrobial agent, and AOT/water. The ratio of AOT to active ranged from 10 to 1000, and the ratio of AOT to water ranged from 1 to approximately 5. In terms of molar amounts of AOT/active, these range from approximately a low value of a 20 molar excess (using CHG and NEO as examples) to that of a 4,500 molar excess (using PHMB as an example). The AOT/active ratio is consistent with additional Aerosol AOT needed to first form a sulfosuccinate salt of the cationic antimicrobial, followed by its dissolution into a sodium bis(2-ethylhexyl)sulfosuccinate (AOT) reverse micelle.

Whereas the biologically-active agents in Table 1 are active through their cationic ion and then solubilized into the anionic bis(2-ethylhexyl)sulfosuccinate reverse micelle, a related study was done with the anionic fatty acid salt sodium laurate (SL) in place of the cationic, biologically-active agents, with anionic AOT as the surfactant. Sodium laurate, the sodium salt of lauric acid, the latter of which is a fatty acid with antibacterial properties, was investigated for its solubility in ISO, a solvent in which it is insoluble, with AOT and water. Solubility of the anionic surfactant occurred giving a clear, homogeneous microemulsion. The ratio of ISO/SL/AOT/$H_2O$ investigated was $92.57/2.78\times10^{-2}/4.63/2.78$, with an AOT/SL ratio of 16.7 and an AOT/$H_2O$ ratio of 1.67, all values consistent with those of Table 1. AOT, an anionic, reverse emulsion surfactant was able to solubilize an anionic, water-soluble fatty acid salt into a microemulsion into the hydrophobic solvent isooctane, thus indicating that both cationic and anionic biological species can be solubilized into a water-in-oil microemulsion.

TABLE 1

Antimicrobial Agents in Isooctane and HMDS, With Aerosol AOT, Water and Ethanol

| Solvent | % Solvent | Active PHMB | Active ALEX | Active CHG | Active NEO | Active $AgNO_3$ | Active $Zn(OAc)_2$ | Active POLYMYX | R-Surf AOT | H20 | EtOH | AOT/ Active | AOT/ H2O |
|---|---|---|---|---|---|---|---|---|---|---|---|---|---|
| ISO | 93.41 | 4.67 × 10−2 | | | | | | | 4.67 | 1.87 | | 100 | 2.5 |
| ISO | 98.31 | | 0.199 × 10−3 | | | | | | 0.497 | 0.198 | | 2500 | 2.5 |
| ISO | 98.68 | | 0.987 × 10−2 | | | | | | 0.493 | 0.493 | 0.326 | 50 | 1 |
| HMDS | 99.40 | 4.97 × 10−4 | | | | | | | 0.497 | 0.099 | | 1000 | 5 |
| HMDS | 94.34 | 4.72 × 10−3 | | | | | | | 4.72 | 0.943 | | 1000 | 5 |
| HMDS | 91.57 | | | 0.183 | | | | | 4.58 | 3.66 | | 25 | 1.25 |

TABLE 1-continued Antimicrobial Agents in Isooctane and HMDS, With Aerosol AOT, Water and Ethanol

| Solvent | % Solvent | Active PHMB | Active ALEX | Active CHG | Active NEO | Active AgNO$_3$ | Active Zn(OAc)$_2$ | Active POLYMYX | R-Surf AOT | H2O | EtOH | AOT/Active | AOT/H2O |
|---|---|---|---|---|---|---|---|---|---|---|---|---|---|
| HMDS | 99.21 | | | | 4.96 × 10−2 | | | | 0.495 | 0.248 | | 10 | 2 |
| HMDS | 93.41 | | | | | 4.67 × 10−2 | | | 4.67 | 1.87 | | 100 | 2.5 |
| HMDS | 92.48 | | | | | 0.116 | | | 4.62 | 2.78 | | 40 | 1.66 |
| HMDS | 92.37 | | | | | | 0.231 | | 4.63 | 2.77 | | 20 | 1.67 |
| HMDS | 93.37 | | | | | | | 9.34 × 10−2 | 4.67 | 1.87 | | 50 | 2.5 |

Table 2 includes other reverse emulsion surfactants that can solubilize the biguanides PHMB and CHG as clear solutions in isooctane or HMDS. These surfactants include Sensiva SC 50 (SC 50, HLB 7.5), Gransurf W9 (G W9, HLB 4.5), and Aerosol TR (TR, HLB 4-7). The amount of surfactant needed to form optically clear, reverse emulsions in ISO and HMDS was substantially higher than that of Table 1, thus reducing the amount of volatile solvent, the latter of which ranged from approximately 48 wt % to 82 wt %. Aerosol TR appeared more effective than Gransurf W9 and Sensiva SC 50, but less effective than Aerosol AOT. The ratio of surfactant to active biguanide agent ranged from 400 to 2000, with a surfactant to water ratio of 10 to 21.

TABLE 2

Antimicrobial Agents in ISO and HMDS with Various Reverse Emulsion Surfactants and Water

| Solvent | % Solvent | Active PHMB | Active CHG | R-Surf G W9 | R-Surf TR | R-Surf SC 50 | H2O | R-Surf/Active | R-Surf/H2O |
|---|---|---|---|---|---|---|---|---|---|
| ISO | 48.78 | | 9.76 × 10−2 | 48.78 | | | 2.34 | 500 | 21 |
| HMDS | 48.78 | | 9.76 × 10−2 | 48.78 | | | 2.34 | 500 | 21 |
| HMDS | 81.93 | 4.10 × 10−2 | | | 16.39 | | 1.64 | 400 | 10 |
| HMDS | 47.61 | 2.38 × 10−2 | | | | 47.61 | 4.76 | 2000 | 10 |

Table 3 lists three solid cationic antimicrobial agents (CHG-P, MICON, and GML) and one solid anionic antimicrobial agent (SORB) (anionic at pH above its pK$_a$ of 4.76, http://en.wikipedia.org/wiki/Sorbic acid) in water that are solubilized in HMDS and ISO with a reverse emulsion surfactant and without added water. Chlorhexidine powder (CHG-P) was prepared by the neutralization of chlorhexidine digluconate (CHG), while miconazole nitrate (MICON) and glycerol monolaurate (GML) were used as received. Miconazole is an imidazole-based antifungal agent, and glycerol monolaurate is a monoglyceride with antimicrobial properties. Sorbic acid and its salts are used as preservatives in foods, drugs and preserved solutions, with antimicrobial properties against mold, yeast, and fungi. These biologically active agents were not soluble in isooctane or hexamethyldisiloxane, but were solubilized to give optically clear solutions when four different reverse emulsion surfactants were added (AOT, G W9, G 67(HLB 4.5), and SC 50) to ISO and HMDS. Sorbic acid, a carboxylic acid preservative, was solubilized by Aerosol AOT, an anionic reverse emulsion surfactant, with no difficulty. The solvent concentrations ranged from about 50 to 95 wt %. Although no water was added to the formulations in Table 3, the ratios of surfactant to biologically active agent were similar to those of Tables 1 and 2, ranging from 5 to 500. It is conceivable that trace quantities of water were present in the various components of Table 3 to enhance solubilization.

TABLE 3

Antimicrobial Agents In ISO and HMDS with Various Reverse Emulsion Surfactants and No Added Water

| Solvent | % Solvent | Active % CHG-P | Active % MICON | Active % GML | Active % SORB | R-Surf % AOT | R-Surf % GW9 | R-Sur % G67 | R-Sur % SC 50 | R-Surf/Active |
|---|---|---|---|---|---|---|---|---|---|---|
| HMDS | 95.23 | | 9.52 × 10−2 | | | 4.76 | | | | 50 |
| HMDS | 90.83 | 9.08 × 10−2 | | | | 9.08 | | | | 100 |

TABLE 3-continued

Antimicrobial Agents In ISO and HMDS with Various Reverse Emulsion Surfactants and No Added Water

| Solvent | % Solvent | Active % CHG-P | Active % MICON | Active % GML | Active % SORB | R-Surf % AOT | R-Surf % GW9 | R-Sur % G67 | R-Sur % SC 50 | R-Surf/ Active |
|---|---|---|---|---|---|---|---|---|---|---|
| HMDS | 95.15 | | | 9.51 × 10−2 | | 4.76 | | | | 50 |
| HMDS | 49.95 | 9.99 × 10−2 | | | | | 49.95 | | | 500 |
| ISO | 95.15 | 9.51 × 10−2 | | | | 4.76 | | | | 50 |
| ISO | 95.15 | | | 9.51 × 10−2 | | 4.76 | | | | 50 |
| ISO | 49.95 | 9.99 × 10−2 | | | | | 49.95 | | | 500 |
| ISO | 49.95 | 9.99 × 10−2 | | | | | | 49.95 | | 500 |
| ISO | 94.34 | 0.943 | | | | | | | 4.72 | 5 |
| ISO | 95.15 | | | | 9.52 × 10−2 | 4.76 | | | | 50 |

The formulation of a polymer substrate for controlled release of a biologically active agent from a volatile, non-stinging hydrophobic solvent is illustrated in Table 4. The solvents used were ISO and HMDS, with the antimicrobial agents of PHMB, CHG, NEO, and silver nitrate, in addition to lidocaine hydrochloride, a local anesthetic and antiarrhythmic drug, often used topically to relieve pruritus, burning and pain. The reverse emulsion surfactants included AOT and SC 50.

The polymer substrates used in Table 4 include (1) IOA:NIPAM, a non-crosslinked copolymer of 4:1 parts by weight of isooctyl acrylate (IOA) and N-isopropylacrylamide (NIPAM) monomers; (2) TRIS:MMA, a copolymer of 9:1 parts by weight of 3-methacryloyloxypropyltris(trimethylsiloxy)silane (TRIS) and methyl methacrylate (MMA); (3) Kraton, a commercial elastomer containing block polymers of styrene and ethylene/butylene; (4) Cavilon, 3M™ Cavilon™ No-Sting Barrier Film, a commercial liquid bandage comprised of a proprietary acrylate polymer with polyphenylmethylsiloxane in a volatile solvent of HMDS and ISO; and (5) XL-TRIS, a solubilized, crosslinked polymer of TRIS and methyl methacrylate.

Three polymer-containing solutions were found to not need added water to produce optically clear, homogeneous compositions with the TRIS:NIPAM and Cavilon polymers, while the remaining formulations had ratios of surfactant to water similar to that of Table 1.

Table 4 shows the percent loading of the biologically active agent in the polymer as the volatile solvent has evaporated (% Active in Polymer). These values ranged from 0.01 to 1 wt %.

TABLE 4

| Biologically-Active Agents in a Polymer Matrix with Aerosol AOT and Sensiva SC 50 as Surfactants with and Without Water | | | | | | | | | | | | | | | |
|---|---|---|---|---|---|---|---|---|---|---|---|---|---|---|---|
| Solvent | % Solvent | Polymer | % Polymer | Active % PHMB | Active % CHG | Active % MICON | Active % NEO | Active $AgNO_3$ | Active % LIDO | R-Surf % AOT | R-Surf % SC 50 | % H2O | R-Surf/ Active | R-Surf/ H2O | % Active in Polymer |
| ISO | 89.25 | IOA: NIPAM | 4.46 | 4.46 × 10−2 | | | | | | 4.46 | | 1.78 | 100 | 2.5 | 1 |
| ISO | 89.25 | TRIS: MMA | 4.46 | 4.46 × 10−2 | | | | | | 4.46 | | 1.78 | 100 | 2.5 | 1 |
| ISO | 89.25 | Kraton | 4.46 | 4.46 × 10−2 | | | | | | 4.46 | | 1.78 | 100 | 2.5 | 1 |
| ISO | 94.92 | TRIS: NIPAM | 4.75 | 2.37 × 10−3 | | | | | | 0.237 | | 9.49 × 10−2 | 100 | 2.5 | 0.05 |
| ISO | 94.60 | Cavilon | 4.73 | 4.73 × 10−3 | | | | | | 0.473 | | 0.189 | 100 | 2.5 | 0.1 |
| ISO | 94.60 | TRIS: NIPAM | 4.73 | 4.73 × 10−3 | | | | | | 0.473 | | 0.189 | 100 | 2.5 | 0.1 |
| ISO/ HMDS | 92.44 | Cavilon | 6.96 | 9.94 × 10−4 | | | | | | 0.398 | | 0.199 | 400 | 2 | 0.01 |
| HMDS | 94.86 | TRIS: NIPAM | 4.74 | | 1.897 × 10−2 | | | | | | 0.379 | 0 | 20 | NA | 0.4 |
| ISO/ HMDS | 92.53 | Cavilon | 6.96 | | | 9.95 × 10−3 | | | | 0.497 | | 0 | 50 | NA | 0.1 |
| ISO/ HMDS | 86.11 | Cavilon | 6.48 | | | | 0.463 | | | 4.63 | | 2.31 | 10 | 2 | 7 |
| ISO/ HMDS | 86.87 | Cavilon | 6.54 | | | | | 4.67 × 10−2 | | 4.67 | | 1.87 | 100 | 2.5 | 0.7 |
| ISO/ HMDS | 86.83 | Cavilon | 6.54 | | 9.34 × 10−2 | | | | | 4.67 | | 1.87 | 50 | 2.5 | 1 |
| HMDS | 94.61 | TRIS: NIPAM | 4.73 | | | | | | 2.37 × 10−2 | 0.473 | | 0.167 | 20 | 2.8 | 0.5 |
| HMDS | 94.86 | TRIS: NIPAM | 4.74 | | 1.90 × 10−2 | | | | | | 0.379 | 0 | 20 | NA | 0.4 |
| HMDS | 94.61 | XL-TRIS | 4.73 | | | | | | 4.73 × 10−2 | 0.473 | | 0.142 | 10 | 3.33 | 1 |
| HMDS | 94.61 | Cavilon | 4.73 | | | | | | 4.73 × 10−2 | 0.473 | | 0.142 | 10 | 3.33 | 1 |

Table 5 includes compositions related to Table 4, and provides the solubilities of a combination of antimicrobial agents, CHG and MICON, and PHMB and MICON, in a Cavilon solution solubilized by AOT with water. The ratios of the reverse emulsion surfactant to actives and to water were similar to the other Tables, as was the % loading of the combined antimicrobials in the Cavilon polymer. The compositions of Table 5 were optically clear.

TABLE 5

Combinations of Antimicrobial Agents in a Polymer Matrix with AOT and Water

| Solvent | % Solvent | Polymer | % Polymer | Active % PHMB | Active % CHG | Active % MICON | R-Surf % AOT | % H2O | AOT/ Actives | AOT/ H2O | % Actives in Polymer |
|---|---|---|---|---|---|---|---|---|---|---|---|
| HMDS/ISO | 92.34 | Cavilon | 6.95 |  | 9.93 × 10−3 | 9.93 × 10−3 | 0.496 | 0.199 | 25 | 2.5 | 0.29 |
| HMDS/ISO | 92.23 | Cavilon | 6.91 | 9.62 × 10−4 |  | 9.93 × 10−3 | 0.474 | 0.384 | 45 | 1.2 | 0.15 |

Table 6 lists three compositions that include different medications used in pain therapy: (1) lidocaine (LIDO), (2) pregabalin (PREG), an anticonvulsant drug used for neuropathic pain and anxiety disorders, particularly fibromyalgia and spinal cord injuries, and (3) duloxetine (DULOX), a serotonin-norepinephrine reuptake inhibitor, for peripheral neuropathy, particularly diabetic neuropathy, fibromyalgia, and depressive and anxiety disorders. The solvents were ISO and HMDS, with AOT as the reverse emulsion surfactant with water. The ratios of the surfactant to active and surfactant to water were consistent with other results. The compositions of Table 6 were optically clear.

TABLE 6

Pain Medictions in Isooctane and HMDS, with Aerosol AOT and Water

| Solvent | % Solvent | Active LIDO | Active PREG | Active DULOX | R-Surf AOT | H2O | AOT/Active | AOT/H2O |
|---|---|---|---|---|---|---|---|---|
| ISO | 93.37 |  | 9.34 × 10−2 |  | 4.67 | 1.87 | 50 | 2.5 |
| HMDS | 93.46 | 0.467 |  |  | 4.67 | 1.4 | 10 | 3.33 |
| HMDS | 93.37 |  |  | 9.34 × 10−2 | 4.67 | 1.87 | 50 | 2.5 |

Table 7 shows formulations that include skin penetration enhancers (PE) of isopropyl myristate (IPM) and isopropyl palmitate (IPP), using AOT as the reverse emulsion surfactant in ISO and HMDS containing water, with PHMB and LIDO. Two polymer matrices were studied, XL-TRIS and Cavilon. One formulation had no polymer matrix. The ratios of surfactant to active and surfactant to water were consistent with other Tables. In addition, the ratios of AOT to the penetration enhancers were also studied, and these values show that the penetration enhancer can be used in greater quantity than the reverse emulsion surfactant. The ratio of the penetration enhancer to the active was twice that of the surfactant to the active. The loading of the active in the solvent dried polymer was from 0.025 to 1%. The compositions of Table 7 were optically clear.

TABLE 7

Lidocaine Hydrochloride and PHMB Hydrochloride with a Penetration Enhancer, Aerosol AOT and a Polymer Matrix

| Solvent | % Solvent | Polymer | % Polymer | Active PHMB | Active LIDO | R-Surf AOT | PE IPM | PE IPP | H2O | AOT/ Active | AOT/ H2O | AOT/ PE | PE/ Active | % Active in Polymer |
|---|---|---|---|---|---|---|---|---|---|---|---|---|---|---|
| HMDS | 93.72 | XL-TRIS | 4.69 |  | 4.69 × 10−2 | 0.469 |  | 0.937 | 0.141 | 10 | 3.33 | 0.5 | 20 | 1 |
| HMDS | 93.72 | XL-TRIS | 4.69 |  | 4.69 × 10−2 | 0.469 | 0.937 |  | 0.141 | 10 | 3.33 | 0.5 | 20 | 1 |
| HMDS | 92.85 | XL-TRIS | 4.62 |  | 4.64 × 10−2 | 0.464 | 0.929 | 0.929 | 0.139 | 10 | 3.34 | 0.25 | 40 | 1 |
| ISO | 98.13 |  |  | 2.45 × 10−3 |  | 0.491 |  | 0.98 | 0.393 | 200 | 1.25 | 0.5 | 400 | NA |
| ISO | 89.36 | Cavilon | 8.94 | 2.23 × 10−3 |  | 0.447 | 0.893 |  | 0.357 | 200 | 1.25 | 0.5 | 400 | 0.025 |
| ISO | 93.54 | Cavilon | 4.68 | 2.34 × 10−3 |  | 0.468 | 0.935 |  | 0.374 | 200 | 1.25 | 0.5 | 400 | 0.05 |

Table 8 shows formulations of scopolamine hydrochloride (SCOP) in reverse emulsion surfactants of AOT in ISO or HMDS with water. Scopolamine is a tropane alkaloid drug with muscarinic antagonist effects. It is often used in controlled release patches to prevent nausea and vomiting from motion sickness. The ratios of surfactant to active and surfactant to water are consistent with other Tables. The compositions of Table 8 were optically clear.

TABLE 8

Scopolamine in ISO and HMDS with AOT and Water

| Solvent | % Solvent | Active SCOP | R-Surf AOT | H2O | AOT/ SCOP | AOT/ H2O |
|---|---|---|---|---|---|---|
| ISO | 93.46 | 0.467 | 4.67 | 1.4 | 10 | 3.34 |
| HMDS | 93.46 | 0.467 | 4.67 | 1.4 | 10 | 3.34 |

In Tables 1-8, the HLB values of all reverse emulsion surfactants were within the range of 4-10, a range found for microemulsion reverse surfactants.

The data in the above Tables illustrate that hydrophilic, ionic, polar biologically-active agents can be incorporated into a volatile hydrophobic solvent, which could also include a polymeric substrate for controlled release of the biologically active agent, such that the agent can be transported to and through a surface after evaporation of the volatile solvent. To further demonstrate the delivery properties of biologically-active agents in non-polar, volatile, hydrophobic solvents described herein, antimicrobial analysis by zones of inhibition (ZOI) were undertaken with the Gram positive bacteria, methicillin-resistant *Staphylococcus aureus* (Table 9), the Gram negative bacteria, *Pseudomonas aeruginosa* (Table 10), and the yeast (fungi), *Candida albicans* (Table 11) as a function of time over three days, with various antimicrobials added to Cavilon solution containing AOT. All microbiological testing was done by INCELL Corporation, San Antonio, Tex. All zones of inhibition data were measured in mm.

The zones of inhibition testing for methicillin-resistant *Staphylococcus aureus* and *Pseudomonas aeruginosa* were performed as described below. The bacteria were purchased from ATCC and expanded in Tryptic soy broth overnight. Each of the bacteria cultures was then spread onto Tryptic soy agar (TSA) plates. Sterile cloning cylinders containing the biologically-active agent in a volatile, hydrophobic solvent (0.1 mL per cylinder) were placed on the TSA plates and allowed to air dry for 1 h at room temperature. Neosporin was used as a positive control. The TSA plates were observed and photographed after 24 h, 48 h, and 72 h. Images were used to measure zone of inhibition or areas of clearing surrounding the delivered material.

The zones of inhibition testing was also performed with *Candida albicans*, purchased from ATCC and expanded in Tryptic soy broth overnight. This fungi culture was diluted to 0.1 OD 600 units and spread onto TSA plates. Sterile cloning cylinders were placed on the TSA plates, charged with the biologically-active agent in a volatile, hydrophobic solvent (0.1 mL per cylinder) and allowed to air dry for 1 h at room temperature. A 1% Roccal solution was used as a positive control. The TSA plates were observed and photographed after 24 h, 48 h, and 72 h. Images were used to measure zone of inhibition or areas of clearing surrounding the delivered material.

The polymer substrate chosen for the sustained release studies of biologically-active antimicrobial over time was Cavilon. The Cavilon solution is composed of a proprietary acrylate polymer and a smaller amount of polyphenylmethylsiloxane in HMDS and ISO. This was used as a negative control for all zone of inhibition studies (Tables 8-10).

Table 9 shows the zones of inhibition results for methicillin-resistant *Staphylococcus aureus*, ATCC 700787, with Aerosol AOT, PHMB with AOT, CHX with AOT, NEO with AOT, and silver nitrate with AOT, all in the solids of the Cavilon polymer, determined over a three day period. Similarly, Table 10 provides zones of inhibition results for *Pseudomonas aeruginosa*, ATCC 27853, with Aerosol AOT, PHMB with AOT, CHX with AOT, NEO with AOT, all in the solids of the Cavilon polymer, determined over a three day period. Previously, it was reported that Aerosol AOT (called docusate sodium) was investigated as an antibacterial agent, an antiviral agent, and an antifungal agent. As an antibacterial agent, it was reported active against Gram positive bacteria such as *Staphylococcus aureus*, but was inactive against Gram negative bacteria such as *Pseudomonas aeruginosa* (G. N. Kern, U.S. Pat. No. 4,717,737). As an antifungal agent, AOT was reported effective against *Candida albicans* (G. N. Kern, U.S. Pat. No. 4,885,310).

The ZOI behavior of AOT in Table 9 against methicillin-resistant *Staphylococcus aureus* indicates that AOT in the Cavilon polymer is indeed active against this bacterium, and it was considerably more effective than the Neosporin positive control. In addition, as shown in Table 10, AOT in the Cavilon polymer was considerably more effective against *Pseudomonas aeruginosa* than Neosporin. This behavior is contrary to that expected in view of G. N. Kern (U.S. Pat. No. 4,717,737), whose patent indicated a lack of biocidal activity against Gram negative bacteria, including *Pseudomonas aeruginosa*. Combining AOT with PHMB in the Cavilon polymer substrate significantly enhanced the overall biocidal activity, as its zones of inhibition were significantly greater than AOT alone. Combining AOT with CHG in the Cavilon polymer substrate produced exceptional results, being substantially greater than either the positive control (neomycin) or AOT. This enhanced effect may be due to the higher solubility of CHG in AOT than that of PHMB in AOT, which results in a greater concentration of active in the Cavilon polymer for sustained release. Similarly, silver nitrate and NEO at polymer loadings greater than that of PHMB were also highly effective sustained release antimicrobial agents over the three day period.

TABLE 9

| Zone of Inhibition of *Staphylococcus aureus* with Antimicrobials in AOT and Cavilon | | | | | | | | | | | | | | | |
|---|---|---|---|---|---|---|---|---|---|---|---|---|---|---|---|
| Solvent | % Solvent | % Poly-mer | PC Neo-sporin | Active % PHMB | Active % CHG | Active $AgNO_3$ | Active % NEO | R-Surf % AOT | % H2O | AOT/ Active | AOT/ H2O | % Active in Polymer | ZOI 24 h | ZOI 48 h | ZOI 72 h |
| HMDS/ ISO | 93 | 7 | | | | | | | | | | | 0 | 0 | 0 |
| HMDS/ ISO | 92.54 | 6.97 | | | | | | 0.498 | | | | | 5.34 | 6.3 | 5.32 |

TABLE 9-continued Zone of Inhibition of *Staphylococcus aureus* with Antimicrobials in AOT and Cavilon

| Solvent | % Solvent | % Polymer | PC Neosporin | Active % PHMB | Active % CHG | Active AgNO$_3$ | Active % NEO | R-Surf % AOT | % H2O | AOT/ Active | AOT/ H2O | % Active in Polymer | ZOI 24 h | ZOI 48 h | ZOI 72 h |
|---|---|---|---|---|---|---|---|---|---|---|---|---|---|---|---|
| HMDS/ISO | 92.17 | 6.94 | | 9.91 × 10−4 | | | | 0.496 | 0.396 | 496 | 1.25 | 0.014 | 9.54 | 9.98 | 8.16 |
| HMDS/ISO | 92.26 | 6.94 | | | | | 4.96 × 10−2 | 0.496 | 0.248 | 10 | 2 | 0.71 | 8.95 | 8.94 | 9.71 |
| HMDS/ISO | 92.34 | 6.95 | | | 9.93 × 10−3 | | | 0.496 | 0.199 | 50 | 0.2 | 0.14 | 11.53 | 11.03 | 11.67 |
| HMDS/ISO | 92.35 | 6.95 | | | | 4.97 × 10−3 | | 0.497 | 0.199 | 100 | 2.5 | 0.49 | 8.16 | 9 | 8.18 |
| | | | 100 µL | | | | | | | | | | 3.38 | 3 | 3.19 |

Table 10 shows the zones of inhibition results for *Pseudomonas aeruginosa*. These results show the Cavilon polymer with AOT is a highly effective antibacterial agent over time and substantially better than the Neosporin positive control. This was also found for PHMB and for NEO in AOT and Cavilon polymer. CHG in AOT and Cavilon, however, was less effective, in marked contrast to its activity against *Staphylococcus aureus* (Table 9).

Also of consideration for application to animal and human skin is the potential of toxicity to mammalian cells for reverse emulsion surfactants such as AOT. It has been reported that in water solution, at a concentration as low as 0.002 wt %, AOT is cytotoxic to mammalian cells such as fibroblasts, kidney cells, and cancer cells (G. N. Kern, U.S. Pat. No. 4,885,310). This can be undesirable considering mammalian cells such as

TABLE 10

Zone of Inhibition of *Pseudomonas aeruginosa* with Antimicrobials in AOT and Cavilon

| Solvent | % Solvent | % Polymer | PC Neosporin | Active % PHMB | Active % CHG | Active % NEO | R-Surf % AOT | % H2O | AOT/ Active | AOT/ H20 | % Active in Polymer | ZOI 24 h | ZOI 48 h | ZOI 72 h |
|---|---|---|---|---|---|---|---|---|---|---|---|---|---|---|
| HMDS/ISO | 93 | 7 | | | | | | | | | | 0 | 0 | 0 |
| HMDS/ISO | 92.54 | 6.97 | | | | | 0.498 | | | | | 8.18 | 8.22 | 11.2 |
| HMDS/ISO | 92.17 | 6.94 | | 9.91 × 10−4 | | | 0.496 | 0.396 | 500 | 1.25 | 0.014 | 10.1 | 9.6 | 9.15 |
| HMDS/ISO | 92.34 | 6.95 | | | 9.93 × 10−3 | | 0.496 | 0.199 | 50 | 2.5 | 0.14 | 2.77 | 0 | 0 |
| HMDS/ISO | 92.26 | 6.94 | | | | 4.96 × 10−2 | 0.497 | 0.199 | 10 | 2.5 | 0.71 | 7.43 | 6.41 | 7.61 |
| | | | 100 µL | | | | | | | | | 2.09 | 1.74 | 1.45 |

Table 11 shows zones of inhibition results against of *Candida albicans*, ATCC 10231, for PHMB and MICON in AOT and Cavilon, compared to 1 wt % Roccal as the positive control and Cavilon as the negative control. For the miconazole nitrate formulation, no added water was necessary to solubilize this antifungal agent in AOT. The positive control was superior to all other formulations, perhaps because of its higher concentration. For these data PHMB in AOT appeared slightly less effective than AOT itself. However, MICON with AOT was superior to that of AOT by itself and PHMB with AOT. The ratios of AOT/active and AOT/water were similar to those of other Tables.

fibroblast are needed for wound repair. However, the prior art does not indicate whether AOT is cytotoxic in a volatile, hydrophobic solvent containing polymers for controlled delivery. Therefore, a cytotoxicity studied was conducted using Cavilon solution containing 0.5 wt % AOT, which is a similar concentration to that used in all the above antibacterial and antifungal studies (Tables 9-11). Cavilon solution without AOT was used as a negative control.

The toxicity study was conducted by Toxikon Corporation, Bedford, Mass., and the data is given in Table 12. The biological reactivity of L929 mouse fibroblast cell in response to the AOT Cavilon solution was determined. The monolayer of

TABLE 11

Zone of Inhibitions of *Candida Albicans* with Antimicrobials in AOT and Cavilon

| Solvent | % Solvent | % Polymer | Active % PHMB | Active % MICON | PC % Roccal | R-Surf % AOT | % H2O | AOT/ Active | AOT/ H20 | % Active in Polymer | ZOI 24 h | ZOI 48 h | ZOI 72 h |
|---|---|---|---|---|---|---|---|---|---|---|---|---|---|
| HMDS/ISO | 93 | 7 | | | | 0 | 0 | | | | 0 | 0 | 0 |
| HMDS/ISO | 92.54 | 6.97 | | | | 0.498 | 0 | | | | 12.7 | 12.4 | 13.3 |
| HMDS/ISO | 92.17 | 6.94 | 9.91 × 10−4 | | | 0.496 | 0.396 | 500 | 1.25 | 0.014 | 12.1 | 11.2 | 11.1 |
| HMDS/ISO | 92.53 | 6.96 | | 9.95 × 10−3 | | 0.497 | 0 | 50 | | 0.143 | 16.5 | 14.9 | 15 |
| | | | | | 1 | | | | | | 24.1 | 24 | 23.3 | fibroblasts was cultured in an agar plate, and the cell viability was evaluated using a vital dye (neutral red). The AOT Cavilon solution was applied directly to the surface of the agar. Positive (Buna-N-Rubber) and negative (Negative Control Plastic, Cavilon solution) control articles were prepared to verify the proper functioning of the test system. The cultures were incubated at 37±1° C., in a humidified atmosphere containing 5±1% carbon dioxide. Zone of inhibition was measured, and biological reactivity (cellular degeneration and malformation) was rated on a scale from Grade 0 (No reactivity) to Grade 4 (Severe reactivity) at 24 and 48 hours. The experiment was run in triplicate. The results indicate that AOT Cavilon solution with a Grade of zero, although effective in killing gram positive bacteria, gram negative bacteria, and fungi, is not toxic to mammalian cells.

TABLE 12

Cytotoxicity Testing of 0.5 wt % AOT in Cavilon

| Time | 0.05 wt % AOT in Cavilon | | Positive Control | | Negative Control | | Disc Control | |
|---|---|---|---|---|---|---|---|---|
| | Zone Size (cm) | Grade | Zone Size (cm) | Grade | Zone Size (cm) | Grade | Zone Size (cm) | Grade |
| 24 hours | 0 | 0 | 0.3 | 3 | 0 | 0 | 0 | 0 |
| 48 hours | 0 | 0 | 0.3 | 3 | 0 | 0 | 0 | 0 |

Another concern with the use of a reverse emulsion surfactant for its application to mammalian skin is its potential to cause skin irritation. It has been reported that in water solution AOT can be irritating to skin (M. Changez and M. Varshney, Drug Development and Industrial Pharmacy, 26(5), 507-512 (2000)). To test if AOT is skin-irritating when used in a volatile, hydrophobic solvent with the presence of polymer, an animal skin-irritation study was conducted by Toxikon Corporation, Cavilon solution containing 0.5 wt % AOT was examined, and Cavilon solution was used as a negative control.

Three albino rabbits were used for the skin irritation study. The application sites were prepared by clipping the skin of the trunk free of hair within 24 h before application of the test and control substances. The animals were treated by applying an AOT-containing Cavilon solution and the Cavilon negative control (0.5 mL) directly onto skin over a skin area of approximate 6 cm$^2$. The test solution was applied to the skin on the left side of the spine and the control solution was applied to the skin on the right side of the spine. The AOT solution and the negative control were each applied sequentially to three sites, and observed at 6, 24, 48, and 72 h for signs of erythema and edema. Observations were scored according to the Draize Scale for Scoring. None of the AOT solution sites presented any signs of erythema or edema at any of the observation points. None of the control sites of any animal at any of the observation periods showed signs of erythema or edema. Therefore, the tested AOT Cavilon solution was considered a non-irritant.

Other Embodiments

While the above specification contains many specifics, these should not be construed as limitations on the scope of the invention, but rather as examples of preferred embodiments thereof. Many other variations are possible. Accordingly, the scope of the invention should be determined not by the embodiments illustrated, but by the appended claims and their legal equivalents.

We claim:

1. A composition comprising:
    a reverse microemulsion comprising at least one hydrophilic, biologically-active agent solubilized by a hydrophobic reverse emulsion surfactant in a non-stinging, volatile, hydrophobic solvent, and
    a polymer substrate soluble in the non-stringing, volatile, hydrophobic solvent,
    wherein said non-stinging, volatile, hydrophobic solvent is selected from the group consisting of volatile linear and cyclic siloxanes, volatile linear, branched and cyclic alkanes, and combinations thereof.

2. The composition according to claim 1, wherein the reverse microemulsion is an optically clear solution.

3. The composition according to claim 1, wherein said reverse emulsion surfactant is selected from the group comprising sodium bis(2-ethylhexyl)sulfosuccinate, sodium bis(tridecyl)sulfosuccinate, bis(dialkyl)sulfosuccinate salts, copolymers of polydimethylsiloxane and polyethylene/polypropylene-oxide, polyoxypropylene (12) dimethicone, cetyl PEG/PPG-10/1 dimethicone, hexyl laurate and polyglyceryl-4-isostearate, PEG-10 dimethicone, sorbitan monolaurate, sorbitan monooleate, polyoxyethylenesorbitan trioleate, polyoxyethylene octyl phenyl ether, polyoxyethylene cetyl ether, polyethylene glycol tert-octylphenyl ether, sodium di(2-ethylhexyl)phosphate, sodium di(oleyl)phosphate, sodium di(tridecyl)phosphate, sodium dodecylbenzenesulfonate, sodium 3-dodecylaminopropanesulfonate, sodium 3-dodecylaminopropionate, sodium N-2-hydroxydodecyl-N-methyltaurate, lecithin, sucrose fatty acid esters, 2-ethylhexylglycerin, caprylyl glycol, long chain hydrophobic vicinal diols of monoalkyl glycols, monoalkyl glycerols, or monoacyl glycerols, polyoxyl castor oil derivatives, polyethylene glycol hydrogenated castor oil, potassium oleate, sodium oleate, cetylpyridynium chloride, alkyltrimethylammonium bromides, benzalkonium chloride, didodecyldimethylammonium bromide, trioctylmethylammonium bromide, cetyltrimethylammonium bromide, cetyldimethylethylammonium bromide, and combinations thereof.

4. The composition according to claim 1, wherein the reverse emulsion surfactant is sodium bis(2-ethylhexyl)sulfosuccinate.

5. The composition according to claim 1, wherein said non-stinging, volatile, hydrophobic solvent comprises at least one of hexamethyldisiloxane, octamethylcyclotetrasiloxane, decamethylcyclopentasiloxane, octamethyltrisiloxane, propane, isobutane, butane (under pressure), pentane, hexane, heptane, octane, isooctane, petroleum distillates, and cyclohexane.

6. The composition according to claim 1, wherein said non-stinging, volatile, hydrophobic solvent comprises a solvent selected from the group consisting of hexamethyldisiloxane, isooctane, isobutane, butane (under pressure), pentane, hexane, heptane, octane, and isomers thereof, petroleum distillates, cyclohexane, and mixtures thereof.

7. The composition according to claim 1, wherein the polymer substrate soluble is present in an amount ranging from 1 to 20 weight percent.

8. The composition according to claim 7, wherein the polymer substrate is selected from the group consisting of (i) siloxy-containing polymers of 3-methacryloyloxypropyltris(trimethylsiloxy)silane (TRIS), methyl methacrylate, N-isopropylacrylamide, 1,3-bis(3-methacryloyloxypropyl)-1,1,3,3-tetrakis(trimethylsiloxy)disiloxane (TRIS dimer), (ii) polymers and copolymers of isooctyl acrylate, (iii) block copolymers of polydimethylsiloxane and polyurethanes, (iv)

block copolymers of polydimethylsiloxane and poly(ethylene glycol), (v) block copolymers of polystyrene and ethylene/butylene, (vii) block copolymers of polystyrene and polyisobutylene, (viii) butyl rubber, (ix) polyisobutylene, (x) polymers and copolymers of $C_4$-$C_{18}$ acrylates and methacrylates, (xi) and combinations thereof.

9. The composition according to claim 1, further comprising a penetration enhancer.

10. The composition according to claim 9, wherein the penetration enhancer is selected from the group consisting of $C_6$-$C_{18}$ saturated acids, branched and linear, $C_{14}$ to $C_{22}$ unsaturated acids, oleic acid, cis-9-octadecenoic acid, linoleic acid, linolenic acid, $C_8$-$C_{18}$ saturated fatty, terpenes, d-limonene, alpha-pinene, 3-carene, menthone, fenchone, pulegone, piperitone, eucalyptol, chenopodium oil, carvone, menthol, alpha-terpineol, terpinen-4-ol, carveol, limonene oxide, pinene oxide, cyclopentane oxide, cyclohexane oxide, ascaridole, 7-oxabicylco[2,2,1]heptane, 1,8-cineole, glycerol monoethers, glycerol monolaurate, glycerol monooleate, 2-pyrrolidone, N-methyl-2-pyrrolidone, 1-ethyl-2-pyrrolidone, 5-methyl-2-pyrrolidone, 1,5-dimethyl-2-pyrrolidone, 2-pyrrolidone-5-carboxylic acid, N-hexyl-2-pyrrolidone, N-lauryl-2-pyrrolidone, 4-decyloxazolidin-2-one, 1-dodecylazacycloheptan-2-one, N-dodecylcaprolactam, and 1-methyl-3-dodecyl-2-pyrrolidone, alkyltrimethylammonium halides, alkyldimethylbenzylammonium halides, alkylpyridinium halides, sodium lauryl sulfate, polysorbates 20, 21, 80 and 81, Pluronic F127, Pluronic F68, N-n-butyl-N-n-dodecylacetamide, N,N-di-n-dodecylacetamide, N-cycloheptyl-N-n-dodecylacetamide and N,N-di-n-propyldodecanamide, urea, 1-dodecylurea, 1,3-didodecylurea, 1,3-diphenylurea, dimethyl sulfoxide, decylmethyl sulfoxide, tetradecylmethyl sulfoxide, methyl laureate, isopropyl lanolate, isopropyl myristate, isopropyl palmitate, cyclodextrins, 1-alkyl-2-piperidinones, 1-dodecyazacycloheptan-2-one, 1,2,3-alkanetriols, 1,2,3-nonanetriol, 1,2-alkanediols, n-alkyl-β-D-glucopyranosides, 2-(1-alkyl)-2-methyl-1,3-dioxolanes, oxazolidinones, 4-decyloxazolidin-2-one, N,N-dimethylalkanamides, 1,2-dihydroxypropyl alkanoates, 1,2-dihydroxypropyl decanoate, 1,2-dihydroxypropyl octanoate, sodium deoxycholate, trans-3-alken-1-ols, cis-3-alken-1-ols, and trans-hydroxyproline-N-alkanamide-C-ethylamide.

11. The composition according to claim 9, wherein the penetration enhancer is selected from isopropyl myristate, isopropyl palmitate, and combinations thereof.

12. The composition comprising:
a reverse micoemulsion comprising at least one hydrophilie, biologically-active agent solubilized by a hydrophobic reverse emulsion surfactant in a non-stinging, volatile, hydrophobic solvent,
wherein said non-stinging, volatile, hydrophobic solvent is selected from the group consisting of volatile linear and cyclic siloxanes, volatile linear, branched and cyclic alkanes, volatile fluorocarbons and chlorofluorocarbons, liquid carbon dioxide under pressure, and combinations thereof, comprising from 40-90 weight percent volatile, hydrophobic solvent, from 0.25 to 50 weight percent reverse emulsion surfactant, from 0.00001 to 5 weight percent of biologically active agent, and a polymer substant soluble in the non-stinging, volatile, hydrophobic solvent, wherein the polymer substrant is present in an amount less than 20 weight percent.

13. The composition according to claim 1, comprising less than 3 weight percent hydrophilic solvents selected from the group consisting of water, $C_1$-$C_4$ alkyl alcohols, and mixtures thereof.

14. The composition according to claim 1, wherein a weight ratio of reverse emulsion surfactant to biologically active agent ranges from 1 to 3,000.

15. The composition according to claim 1, wherein the biologically active agent is an antimicrobial selected from the group consisting of poly(hexamethylene biguanide) hydrochloride and related salts, alexidine hydrochloride and related salts, chlorhexidine digluconate, chlorhexidine diacetate and related salts, nanosilver, colloidal silver, silver sulfadiazine, silver nitrate, hydrogen peroxide, benzoyl peroxide, peracetic acid, lactic acid, fatty acids, ethanol, isopropanol, long-chain alcohols, branched and long-chain glycols, glycerol ethers and esters, essential oils, benzalkonium chloride, benzethonium chloride, methylbenzethonium chloride, cetyltrimethylammonium bromide, cetylpyridinium chloride, honey, boric acid, benzoic acid, povidone-iodine, poloxamer-iodine, iodine, salicylic acid, zinc salts, tin salts, aluminum sulfate, bismuth subsalicylate, clotrimazole, miconazole nitrate, ketoconazole, fluconazole, oxiconazole nitrate, methyl salicylate, triethanolamine salicylate, phenyl salicylate, acetylsalicylic acid, thymol, eucalyptol, menthol, eugenol, peppermint oil, sage oil, chloroxlyneol, cloflucarban, hexylresorcinol, triclocarban, hexachlorophene, pyrithione zinc, chlorobutanol, capsaicin, warfarin, bacitracin, neomycin sulfate, polymyxin b sulfate, aloe vera, glutaraldehyde, formaldehyde, ethylene oxide, chloroamines, Dakin's solution, dilute bleach, polyquaternium-1, polyquaternium-10, ionene polymers, pyridinium polymers, imidazolium polymers, diallyldimethylammonium polymers, acryloyl-, methacryloyl-, and styryl-trimethylammonium polymers, acrylamido- and methacrylamido-trimethylammonium polymers, antimicrobial peptides, and combinations thereof.

16. The composition according to claim 1, wherein the biologically-active agent is a pharmaceutical selected from the group consisting of 9-lactam antibiotics, penicillins, and ampicillin, ampicillin-sublactam, nafcillin, amoxicillin, cloxacillin, methicillin, oxacillin, dicloxacillin, azocillin, bacampicillin, cyclacillin, carbenicillin, carbenicillin indanyl, mezlocillin, penicillin G, penicillin V, ticarcillin, piperacillin, aztreonam and imipenem, cephalosporins, cephapirin, cefaxolin, cephalexin, cephradine, cefadroxil, cefamandole, cefoxitin, cefaclor, cefuroxime, cefuroxime axetil, cefonicid, cefotetan, ceforanide, cefotaxime, ceftizoxime, ceftriaxone, cefoperazone and ceftazidime, tetracyclines, demeclocytetracycline, doxycycline, methacycline, minocycline, oxytetracycline, beta-lactamase inhibitors, clavulanic acid, aminoglycosides, amikacin, gentamicin C, kanamycin A, neomycin B, netilmicin, streptomycin, tobramycin, erythromycin, clindamycin, spectinomycin, vancomycin, bacitracin, isoniazid, rifampin, ethambutol, aminosalicylic acid, pyrazinamide, ethionamide, cycloserine, dapsone, sulfoxone sodium, clofazimine, sulfonamides, sulfanilamide, sulfamethoxazole, sulfacetamide, sulfadiazine, sulfisoxazole, trimethoprim-sulfamethoxazole, quinolones, nalidixic acid, cinoxacin, norfloxacin, ciprofloxacin, methenamine, nitrofurantoin and phenazopyridine, chloroquine, emetine, dehydroemetine, 8-hydroxyquinolines, metronidazole, quinacrine, melarsoprol, nifurtimox, pentamidine, amphotericin-B, flucytosine, ketoconazole, miconazole, itraconazole, griseofulvin, clotrimazole, econazole, terconazole, butoconazole, ciclopirox olamine, haloprogin, toinaftate, naftifine, nystatin, natamycin, undecylenic acid, benzoic acid, salicylic acid, propionic acid, caprylic acid, zidovudine, acyclovir, ganciclovir, vidarabine, idoxuridine, trifluridine, foxcarnet, amantadine, rimantadine, tee tree oil, ribavirin, metronidiazole, mebendazole, albendazole, milbemycin, ivermectin, praziquantel, artemisinin, quinine, chloroquine, halofantrine, mefloquine, lumefantrine, amodiaquine, pyronaridine, piperaquine, primaquine, tafenoquine, atovaquone, artemether, artesunate, dihydroartemisinin, artemisinin, proguanil, tetracyclines, pentamidine, suramin, melarsoprol, amphotericin, eflornithine, benznidazole, aminosidine, nortriptyline, amitriptyline, lidocaine, capsaicin, gabapentin, pregabalin, carbamazepine, duloxetine, venlafaxine, oxycodone, tramadol, nitinol, and combinations thereof.

17. The composition according to claim 1, wherein sodium bis(2-ethylhexyl)sulfosuccinate is the reverse emulsion surfactant and wherein the sodium bis(2-ethylhexyl)sulfosuccinate is an active antimicrobial agent against at least one microbe selected from the group consisting of Gram negative bacteria, Gram positive bacteria, and fungi.

18. The composition according to claim 1, wherein the composition is non-cytotoxic and non-irritating to mammalian cells.

19. A method of forming a polymer coating on a biological surface, comprising applying a composition according to claim 1 to a biological surface.

20. The method according to claim 19, wherein said reverse emulsion surfactant is a dialkylsulfosuccinate salt and said biologically-active agent is an antimicrobial agent.

21. A method according to claim 19 wherein said reverse emulsion surfactant is a dialkylsulfosuccinate salt and said biologically-active agent is an antibiotic agent.

22. A method of delivering a biologically-active agent to a biological surface, comprising applying a composition according to claim 1 to a biological surface.

23. The method according to claim 22, wherein said reverse emulsion surfactant is a dialkylsulfosuccinate salt and said biologically-active agent is an antimicrobial agent.

24. A method according to claim 22 wherein said reverse emulsion surfactant is a dialkylsulfosuccinate salt and said biologically-active agent is an antibiotic agent.

25. The method according to claim 22, wherein the polymer substrate is selected from the group consisting of (i) siloxy-containing polymers of 3-methacryloyloxypropyltris(trimethylsiloxy)silane (TRIS), methyl methacrylate, N-isopropylacrylamide, 1,3-bis(3-methacryloyloxypropyl)-1,1,3,3-tetrakis(trimethylsiloxy)disiloxane (TRIS dimer), (ii) polymers and copolymers of isooctyl acrylate, (iii) block copolymers of polydimethylsiloxane and polyurethanes, (iv) block copolymers of polydimethylsiloxane and poly(ethylene glycol), (v) block copolymers of polystyrene and ethylene/butylene, (vii) block copolymers of polystyrene and polyisobutylene, (viii) butyl rubber, (ix) polyisobutylene, (x) polymers and copolymers of $C_4$-$C_{18}$ acrylates and methacrylates, (xi) and combinations thereof.

* * * * *